US007225032B2

(12) United States Patent
Schmeling et al.

(10) Patent No.: US 7,225,032 B2
(45) Date of Patent: May 29, 2007

(54) EXTERNAL POWER SOURCE, CHARGER AND SYSTEM FOR AN IMPLANTABLE MEDICAL DEVICE HAVING THERMAL CHARACTERISTICS AND METHOD THEREFORE

(75) Inventors: Andrew L. Schmeling, River Falls, WI (US); William C. Phillips, Brooklyn Park, MN (US); David P. Olson, Minnetrista, MN (US); Oscar Jimenez, Coral Gables, FL (US)

(73) Assignee: Medtronic Inc., Minneapolis, MN (US)

( * ) Notice: Subject to any disclaimer, the term of this patent is extended or adjusted under 35 U.S.C. 154(b) by 382 days.

(21) Appl. No.: 10/836,101

(22) Filed: Apr. 30, 2004

(65) Prior Publication Data

US 2005/0075694 A1   Apr. 7, 2005

Related U.S. Application Data

(60) Provisional application No. 60/508,097, filed on Oct. 2, 2003.

(51) Int. Cl.
*A61N 1/00*   (2006.01)
(52) U.S. Cl. .............................. 607/61; 607/33; 607/36
(58) Field of Classification Search .................. 607/61, 607/62; 320/150–153
See application file for complete search history.

(56) References Cited

U.S. PATENT DOCUMENTS

| 3,357,434 | A | 12/1967 | Abell |
| 3,888,260 | A | 6/1975 | Fischell |
| 4,014,346 | A | 3/1977 | Brownlee et al. |
| 4,041,955 | A | 8/1977 | Kelly et al. |
| 4,071,032 | A | 1/1978 | Schulman |
| 4,134,408 | A | 1/1979 | Brownlee et al. |

(Continued)

FOREIGN PATENT DOCUMENTS

EP   0 619 123   10/1994

(Continued)

OTHER PUBLICATIONS

International Search Report for International Application No. PCT/US2004/029830.

(Continued)

*Primary Examiner*—Robert E. Pezzuto
*Assistant Examiner*—Brian T. Gedeon
(74) *Attorney, Agent, or Firm*—IPLM Group, P.A.

(57) ABSTRACT

External power source, charger, system and method for transcutaneous energy transfer. An implantable medical device has a first housing having operational componentry for providing the therapeutic output. A secondary housing is mechanically coupled to the first housing having a secondary coil operatively coupled to the componentry, the secondary coil capable of receiving energy from the external source. A magnetically shielding material is positioned between the secondary coil and the first housing. An external power source has an external housing. A primary coil carried in the external housing, the primary coil being capable of inductively energizing the secondary coil when the housing is externally placed in proximity of the secondary coil with a first surface of the housing positioned closest to the secondary coil, the first surface of the housing being thermally conductive surface. An energy absorptive material carried within the external housing.

49 Claims, 14 Drawing Sheets

U.S. PATENT DOCUMENTS

| | | | |
|---|---|---|---|
| 4,186,749 A | 2/1980 | Fryer | |
| 4,314,008 A | 2/1982 | Blake | |
| 5,279,292 A | 1/1994 | Baumann et al. | |
| 5,314,457 A | 5/1994 | Jeutter et al. | |
| 5,411,537 A | 5/1995 | Munshi et al. | |
| 5,527,348 A | 6/1996 | Winkler et al. | |
| 5,562,714 A | 10/1996 | Grevious | |
| 5,613,935 A | 3/1997 | Jarvik | |
| 5,690,693 A | 11/1997 | Wang et al. | |
| 5,702,431 A | 12/1997 | Wang et al. | |
| 5,713,939 A | 2/1998 | Nedungadi et al. | |
| 5,733,313 A | 3/1998 | Barreras, Sr. et al. | |
| 5,861,019 A | 1/1999 | Sun et al. | |
| 5,919,211 A | 7/1999 | Adams | |
| 5,991,665 A * | 11/1999 | Wang et al. | 607/61 |
| 6,067,474 A * | 5/2000 | Schulman et al. | 607/57 |
| 6,154,677 A | 11/2000 | Leysieffer | |
| 6,178,353 B1 | 1/2001 | Griffith et al. | |
| 6,275,737 B1 | 8/2001 | Mann | |
| 6,308,101 B1 | 10/2001 | Faltys et al. | |
| 6,324,430 B1 | 11/2001 | Zarinetchi et al. | |
| 6,324,431 B1 | 11/2001 | Zarinetchi et al. | |
| 6,496,733 B2 | 12/2002 | Zarinetchi et al. | |
| 6,505,077 B1 | 1/2003 | Kast et al. | |
| 6,516,227 B1 | 2/2003 | Meadows et al. | |
| 6,586,912 B1 | 7/2003 | Tsukamoto et al. | |
| 2002/0032472 A1 | 3/2002 | Zarinetchi et al. | |
| 2002/0038138 A1 | 3/2002 | Zarinetchi et al. | |
| 2003/0171792 A1 | 9/2003 | Zarinetchi et al. | |
| 2003/0208244 A1 | 11/2003 | Stein et al. | |
| 2004/0015198 A1 | 1/2004 | Skarstad et al. | |
| 2004/0058186 A1 | 3/2004 | Daulton | |
| 2004/0059392 A1 | 3/2004 | Parramon et al. | |
| 2004/0088032 A1 | 5/2004 | Haller et al. | |
| 2004/0098068 A1 | 5/2004 | Carbunaru et al. | |
| 2004/0106963 A1 | 6/2004 | Tsukamoto et al. | |
| 2004/0172090 A1 | 9/2004 | Janzig et al. | |
| 2004/0176814 A1 | 9/2004 | Singhai et al. | |
| 2004/0176816 A1 | 9/2004 | Singhai et al. | |
| 2004/0176819 A1 | 9/2004 | Wahlstrand et al. | |

FOREIGN PATENT DOCUMENTS

| | | |
|---|---|---|
| EP | 0 811 395 A2 | 12/1997 |
| EP | 0 811 395 A3 | 12/1997 |
| EP | 1 048 324 A2 | 11/2000 |
| EP | 1 424 098 | 6/2004 |
| WO | WO 96/40367 | 12/1996 |
| WO | WO 98/11942 | 3/1998 |
| WO | WO 98/37926 | 9/1998 |
| WO | WO 99/06108 | 2/1999 |
| WO | WO 99/42173 | 8/1999 |
| WO | WO 99/44684 | 9/1999 |
| WO | WO 00/01442 | 1/2000 |
| WO | WO 01/28622 | 4/2001 |
| WO | WO 01/83029 A1 | 11/2001 |
| WO | WO 01/97908 A2 | 12/2001 |
| WO | WO 01/97908 A3 | 12/2001 |
| WO | WO 2004/02572 | 1/2004 |
| WO | WO 2004/009179 | 1/2004 |

OTHER PUBLICATIONS

Medtronic, Inc. "Implantable Neurostimulation Systems", 1998.

Sinha, Gunjan, "The Heart, Medicine & Health", Popular Science, p. 43, Feb. 2000.

Medtronic, Inc. "Mattrix Neurostimulation System", Brochure, 1995.

* cited by examiner

EXTERNAL POWER SOURCE, CHARGER AND SYSTEM FOR AN IMPLANTABLE MEDICAL DEVICE HAVING THERMAL CHARACTERISTICS AND METHOD THEREFORE

FIELD OF THE INVENTION

This invention relates to implantable medical devices and, in particular, to energy transfer devices, systems and methods for implantable medical devices.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function whether it be driving an electrical infusion pump, providing an electrical neurostimulation pulse or providing an electrical cardiac stimulation pulse. This electrical power is derived from a power source.

Typically, a power source for an implantable medical device can take one of two forms. The first form utilizes an external power source that transcutaneously delivers energy via wires or radio frequency energy. Having electrical wires which perforate the skin is disadvantageous due, in part, to the risk of infection. Further, continuously coupling patients to an external power for therapy is, at least, a large inconvenience. The second form utilizes single cell batteries as the source of energy of the implantable medical device. This can be effective for low power applications, such as pacing devices. However, such single cell batteries usually do not supply the lasting power required to perform new therapies in newer implantable medical devices. In some cases, such as an implantable artificial heart, a single cell battery might last the patient only a few hours. In other, less extreme cases, a single cell unit might expel all or nearly all of its energy in less than a year. This is not desirable due to the need to explant and re-implant the implantable medical device or a portion of the device. One solution is for electrical power to be transcutaneously transferred through the use of inductive coupling. Such electrical power or energy can optionally be stored in a rechargeable battery. In this form, an internal power source, such as a battery, can be used for direct electrical power to the implanted medical device. When the battery has expended, or nearly expended, its capacity, the battery can be recharged transcutaneously, via inductive coupling from an external power source temporarily positioned on the surface of the skin.

Several systems and methods have been used for transcutaneously inductively recharging a rechargeable used in an implantable medical device.

U.S. Pat. No. 5,411,537, Munshi et al, Rechargeable Biomedical Battery Powered Devices With Recharging and Control System Therefor, (Intermedics, Inc.) discloses a hermetically-sealed automatic implantable cardioverter-defibrillator (AICD) or any other bioimplantable device which may be operated on a single rechargeable cell, or a dual power source system, the rechargeable complement being recharged by magnetic induction. Included in the implantable devices are lithium rechargeable chemistries designed to sense the state-of-charge or discharge of the battery; a battery charge controller specifically designed to recharge a lithium battery rapidly to less than 100% full charge, and preferably 90%, more preferably 80%, of full rated charge capacity; and charging means for multi-step charging. The batteries are based on lithium chemistries specially designed to yield higher currents than conventional primary lithium chemistries and to permit long-term performance despite sub-capacity recharging.

U.S. Pat. No. 5,690,693, Wang et al, Transcutaneous Energy Transmission Circuit For Implantable Medical Device, (Sulzer Intermedics Inc.) discloses a transcutaneous energy transmission device for charging rechargeable batteries in an implanted medical device. A current with a sinusoidal waveform is applied to a resonant circuit comprising a primary coil and a capacitor. Current is induced in a secondary coil attached to the implanted medical device. Two solid-state switches are used to generate the sinusoidal waveform by alternately switching on and off input voltage to the resonant circuit. The sinusoidal waveform reduces eddy current effects in the implanted device which detrimentally increases the temperature of the implanted device. The batteries are charged using a charging protocol that reduces charging current as the charge level in the battery increases. The controller is constructed as a pulse with modulation device with a variable duty cycle to control the current level applied to the primary coil. An alignment indicator is also provided to insure proper and alignment between the energy transmission device and the implanted medical device.

U.S. Pat. No. 5,733,313, Barreras, Sr., RF Coupled Implantable Medical Device With Rechargeable Back-Up Power Source, (Exonix Corporation) discloses an implantable, electrically operated medical device system having an implanted radio frequency (RF) receiving unit (receiver) incorporating a back-up rechargeable power supply and an implanted, electrically operated device, and an external RF transmitting unit (transmitter). RF energy is transmitted by the transmitter and is coupled into the receiver which is used to power the implanted medical device and/or recharge the back-up power supply. The back-up power supply within the receiver has enough capacity to be able to, by itself, power the implanted device coupled to the receiver for at least 24 hours during continual delivery of medical therapy. The receiver is surgically implanted within the patient and the transmitter is worn externally by the patient. The transmitter can be powered by either a rechargeable or non-rechargeable battery. In a first mode of operation, the transmitter will supply power, via RF coupled energy, to operate the receiver and simultaneously recharge the back-up power supply. In a second mode of operation, the receiver can, automatically or upon external command from the transmitter, acquire its supply of power exclusively from the back-up power supply. Yet, in a third mode of operation, the receiver can, automatically or upon command from the transmitter, alternatively acquire it supply of power from either, FR energy coupled into the receiver or the internal back-up power supply.

U.S. Pat. No. 6,308,101, Faltys et al, Fully Implantable Cochlear Implant System, (Advanced Bionics Corporation) discloses a fully implantable cochlear implant system and method including an implantable cochlear stimulator unit that is connected to an implantable speech processor unit.

Both the speech processor unit and the cochlear stimulator unit are in separate, hermetically-sealed, cases. The cochlear stimulator unit has a coil permanently connected thereto through which magnetic or inductive coupling may occur with a similar coil located externally during recharging, programming, or externally-controlled modes of operation. The cochlear stimulator unit further has a cochlear electrode array permanently connected thereto via a first multi-conductor cable. The cochlear stimulator unit also has a second multi-conductor cable attached thereto, which second cable contains no more than five conductors. The second cable is detachably connected to the speech processor unit. The speech processor unit includes an implantable subcutaneous microphone as an integral part thereof, and further includes speech processing circuitry and a replenishable power source, e.g., a rechargeable battery.

U.S. Pat. No. 6,324,430, Zarinetchi et al, Magnetic Shield For Primary Coil of Transcutaneous Energy Transfer Device, (Abiomed, Inc.) discloses a transcutaneous energy transfer device which has a magnetic shield covering the primary winding of the device to reduce sensitivity of the device to conducting objects in the vicinity of the coils and to increase the percentage of magnetic field generated by the primary coil which reaches the secondary coil. The shield is preferably larger than the primary coil in all dimensions and is either formed of a high permeability flexible material, for example a low loss magnetic material and a flexible polymer matrix, with perforations formed in the material sufficient to permit ventilation of the patient's skin situated under the shield, or the shield may be formed of segments of a very high permeability material connected by a flexible, porous mesh material.

U.S. Pat. No. 6,516,227, Meadows et al, Rechargeable Spinal Cord Stimulator System, (Advanced Bionics Corporation) discloses a spinal cord stimulation system providing multiple stimulation channels, each capable of producing up to 10 milliamperes of current into a one kilohm load. The system further includes a replenishable power supply, e.g., a rechargeable battery that requires only an occasional recharge, and offers a life of at least 10 years at typical settings. The replenishable power source may be replenished using non-invasive means. The system monitors the state of charge of the internal power source and controls the charging process by monitoring the amount of energy used by the system, and hence the state of the charge of power source. A suitable bidirectional telemetry link allows the system to inform the patient or clinician regarding the status of the system, including the state of the charge, and makes requests to initiate an external charge process.

U.S. Pat. No. 6,505,077, Kast et al, Implantable Medical Device With External Recharging Coil Electrical Connection, (Medtronic, Inc.) discloses a rechargeable implantable medical device with an improved external recharging coil electrical connection resistant to corrosion. The electrical connection couples the external recharging coil to a recharge feedthrough. The rechargeable implantable medical device can be a medical device such as a neuro stimulator, drug delivery pump, pacemaker, defibrillator, diagnostic recorder, cochlear implant, and the like. The implantable medical device has a housing, electronics carried in the housing configured to perform a medical therapy, a rechargeable power source, and a recharging coil.

European Patent Application 1,048,324, Schallhorn, Medical Li+ Rechargeable Powered Implantable Stimulator, (Medtronic, Inc.) discloses an implantable stimulator having a rechargeable lithium ion power source and delivers electrical stimulation pulses, in a controlled manner, to a targeted site within a patient. The lithium ion power source can supply sufficient power to the implantable stimulator on an exclusive basis over at least about 4 days. The power source includes a high value, small size lithium ion storage unit having a power rating of at least 50 milliamp hours. The implantable stimulator also has an inductor adapted to gather EMF power transmissions. The implantable stimulator can be replenished with electrical power by an electrical power replenisher, external to the implantable stimulator, to replenish the lithium ion power source up to its maximum rated voltage by generating the EMF power transmission near the inductor.

PCT Patent Application No. WO 01/83029 A1, Torgerson et al, Battery Recharge Management For an Implantable Medical Device, (Medtronic, Inc.) discloses an implantable medical device having an implantable power source such as a rechargeable lithium ion battery. The implantable medical device includes a recharge module that regulates the recharging process of the implantable power source using closed-loop feedback control. The recharging module includes a recharge regulator, a recharge measurement device monitoring at least one recharge parameter, and a recharge regulation control unit for regulating the recharge energy delivered to the power source in response to the recharge measurement device. The recharge module adjusts the energy provided to the power source to ensure that the power source is being recharged under safe levels.

PCT Patent Application No. WO 01/97908 A2, Jimenez et al, An Implantable Medical Device With Recharging Coil Magnetic Shield, (Medtronic, Inc.) discloses a rechargeable implantable medical device with a magnetic shield placed on the distal side of a secondary recharging coil to improve recharging efficiency. The rechargeable implantable medical device can be wide variety of medical devices such as neurostimulators, drug delivery pumps, pacemakers, defibrillators, diagnostic recorders, and cochlear implants the implantable medical device has a secondary recharging coil carried over a magnetic shield and coupled to electronics and a rechargeable power source carried inside the housing electronics are configured to perform a medical therapy. Additionally a method of for enhancing electromagnetic coupling during recharging of an implantable medical device is disclosed, and a method for reducing temperature rise during recharging of an implantable medical device is disclosed.

Transcutaneous energy transfer through the use of inductive coupling involves the placement of two coils positioned in close proximity to each other on opposite sides of the cutaneous boundary. The internal coil, or secondary coil, is part of or otherwise electrically associated with the implanted medical device. The external coil, or primary coil, is associated with the external power source or external charger, or recharger. The primary coil is driven with an alternating current. A current is induced in the secondary coil through inductive coupling. This current can then be used to power the implanted medical device or to charge, or recharge, an internal power source, or a combination of the two.

For implanted medical devices, the efficiency at which energy is transcutaneously transferred is crucial. First, the inductive coupling, while inductively inducing a current in the secondary coil, also has a tendency to heat surrounding components and tissue. The amount of heating of surrounding tissue, if excessive, can be deleterious. Since heating of surrounding tissue is limited, so also is the amount of energy transfer which can be accomplished per unit time. The higher the efficiency of energy transfer, the more energy can be transferred while at the same time limiting the heating of surrounding components and tissue. Second, it is desirable to limit the amount of time required to achieve a desired charge, or recharge, of an internal power source. While charging, or recharging, is occurring the patient necessarily has an external encumbrance attached to their body. This attachment may impair the patient's mobility and limit the patient's comfort. The higher the efficiency of the energy transfer system, the faster the desired charging, or recharging, can be accomplished limiting the inconvenience to the patient. Third, amount of charging, or recharging, can be limited by the amount of time required for charging, or recharging. Since the patient is typically inconvenienced during such charging, or recharging, there is a practical limit on the amount of time during which charging, or recharging, should occur. Hence, the size of the internal power source can be effectively limited by the amount of energy which can be transferred within the amount of charging time. The higher the efficiency of the energy transfer system, the greater amount of energy which can be transferred and, hence, the greater the practical size of the internal power source. This allows the use of implantable medical devices having higher power use requirements and providing greater therapeutic advantage to the patient and/or extends the time between charging effectively increasing patient comfort.

Prior art implantable medical devices, external power sources, systems and methods have not always provided the best possible control or limitation of temperature build-up while maintaining effective transcutaneous energy transfer and/or charging.

BRIEF SUMMARY OF THE INVENTION

In an embodiment, the present invention provides a system for transcutaneous energy transfer. An implantable medical device has a first housing having operational componentry for providing the therapeutic output. A secondary housing is mechanically coupled to the first housing having a secondary coil operatively coupled to the componentry, the secondary coil capable of receiving energy from the external source. A magnetically shielding material is positioned between the secondary coil and the first housing. An external power source has an external housing. A primary coil carried in the external housing, the primary coil being capable of inductively energizing the secondary coil when the housing is externally placed in proximity of the secondary coil with a first surface of the housing positioned closest to the secondary coil, the first surface of the housing being thermally conductive surface. An energy absorptive material carried within the external housing.

In an embodiment, the present invention provides a system for charging. An implantable medical device has a first housing, a rechargeable power source and operational componentry coupled to the rechargeable power source for providing a therapeutic output. The implantable medical device also has a secondary housing mechanically coupled to the first housing having a secondary coil operatively coupled to the rechargeable power source, the secondary coil capable of receiving energy from the external source. A magnetically shielding material is positioned between the secondary coil and the first housing. The system also has an external charger having an external housing. A primary charging coil is carried in the external housing, the primary charging coil being capable of inductively energizing the secondary coil when the housing is externally placed in proximity of the secondary coil with a first surface of the housing positioned closest to the secondary coil, the first surface of the housing being thermally conductive surface. An energy absorptive material is carried within the external housing.

In another embodiment, the present invention provides an external power source for an implantable medical device having a secondary coil operatively coupled to therapeutic componentry. A primary coil is carried in a housing. The primary coil is capable of inductively energizing the secondary coil when the housing is externally placed in proximity of the secondary coil with a first surface, which is thermally conductive, of the housing positioned closest to the secondary coil.

In another embodiment, the present invention provides an external power source for an implantable medical device having a secondary coil operatively coupled to therapeutic componentry. A primary coil is carried in a housing. The primary coil is capable of inductively energizing the secondary coil when the housing is externally placed in proximity of the secondary coil with a first surface of the housing positioned closest to the secondary coil. A temperature sensor thermally coupled to the first surface.

In a preferred embodiment, the temperature sensor has an accuracy within one-tenth of one degree Centigrade (1° C.) over at least a portion of a range of operation of the temperature sensor.

In a preferred embodiment, the temperature sensor has a high resolution mode and a low resolution mode.

In another embodiment, the present invention provides a system of charging. An implantable medical device has a rechargeable power source and a secondary coil operatively coupled to the rechargeable power source. An external power source has a primary coil carried in a housing. The primary coil is capable of inductively energizing the secondary coil when the housing is externally placed in proximity of the secondary coil with a first surface of the housing positioned closest to the secondary coil. The first surface of the housing is thermally conductive surface.

In another embodiment, the present invention provides a charger for an implantable medical device having a rechargeable power source and a secondary coil operatively coupled to the rechargeable power source. A primary charging coil is carried in the housing. The primary charging coil is capable of inductively energizing the secondary coil when the housing is externally placed in proximity of the secondary coil with a first surface of the housing positioned closest to the secondary coil. The first surface of the housing is a thermally conductive surface.

In another embodiment, the present invention provides a system of transcutaneous energy transfer. An implantable medical device has a secondary coil operatively coupled to therapeutic componentry. An external power source has a primary coil carried in a housing. The primary coil is capable of inductively energizing the secondary coil when the housing is externally placed in proximity of the secondary coil with a first surface, which is thermally conductive, of the housing positioned closest to the secondary coil.

In a preferred embodiment, a temperature sensor thermally coupled to the thermally conductive surface.

In a preferred embodiment, the temperature sensor is capable of indicating a temperature of the thermally conductive surface and further comprising circuitry coupled to the temperature sensor operative to limit the energizing at least in part as a function of the temperature.

In another embodiment, the present invention provides an external power source for an implantable medical device having a secondary coil operatively coupled to therapeutic componentry. A primary coil is carried in the housing, the primary coil being capable of inductively energizing the secondary coil when placed in proximity of the secondary coil. An energy absorptive material is carried within the housing.

In another embodiment, the present invention provides a charger for an implantable medical device having a rechargeable power source and a secondary coil operatively coupled to the rechargeable power source. A primary coil is carried in a housing. The primary charging coil is capable of inductively energizing the secondary coil when placed in proximity of the secondary coil. An energy absorptive material is carried within the housing.

In another embodiment, the present invention provides a system for transcutaneous energy transfer. An implantable medical device has a secondary coil coupled to therapeutic componentry. An external power source is carried in a housing. The primary coil is capable of inductively energizing the secondary coil when placed in proximity of the secondary coil. An energy absorptive material is carried within the housing.

In a preferred embodiment, the energy absorptive material changes state at a temperature near an operating temperature of the housing during operation of the charger.

In a preferred embodiment, the energy absorptive material comprises wax.

In another embodiment, the present invention provides a method of transcutaneous energy transfer from an external power source comprising an external housing and a primary coil carried in the external housing, the primary coil being capable of inductively energizing the secondary coil when the housing is externally placed in proximity of the secondary coil with a first surface of the housing positioned closest to the secondary coil to an implantable medical device comprising a first housing having operational componentry for providing the therapeutic output and a secondary housing mechanically coupled to the first housing having a secondary coil operatively coupled to the componentry, the secondary coil capable of receiving energy from the external source. A magnetically shielding material is positioned between the secondary coil and the first housing. The first surface of the housing is made thermally conductive. An energy absorptive material is carried within the external housing.

In a preferred embodiment, a temperature sensor is thermally coupled to the thermally conductive surface.

In a preferred embodiment, the temperature sensor is capable of indicating a temperature of the thermally conductive surface and further comprising circuitry coupled to the temperature sensor operative to limit the energizing at least in part as a function of the temperature.

In a preferred embodiment, the temperature has a high resolution mode and a low resolution mode.

In a preferred embodiment, the external power source limits the energizing above a predetermined temperature of the thermally conductive surface and wherein the circuitry utilizes the high resolution mode of the temperature sensor when the temperature of the thermally conductive surface is within three degrees Celsius of the predetermined temperature and utilizes the low resolution mode of the temperature sensor when the temperature of the thermally conductive surface is outside of three degrees Celsius of the predetermined temperature.

DETAILED DESCRIPTION OF THE INVENTION

Figure 1:
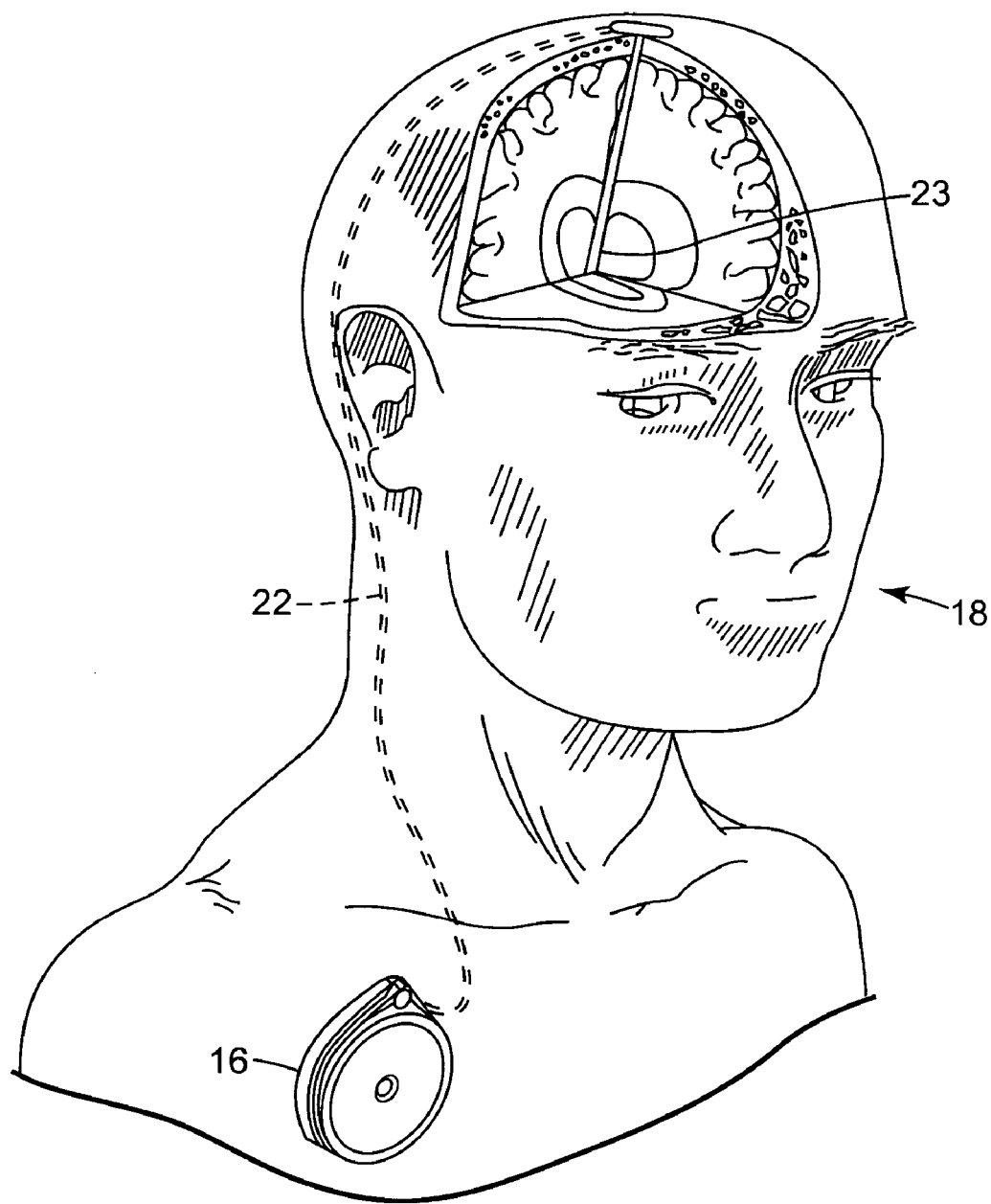
FIG. 1 illustrates an implantable medical device implanted in a patient.

FIG. 1 shows implantable medical device 16, for example, a drug pump, implanted in patient 18. The implantable medical device 16 is typically implanted by a surgeon in a sterile surgical procedure performed under local, regional, or general anesthesia. Before implanting the medical device 16, a catheter 22 is typically implanted with the distal end position at a desired therapeutic delivery site 23 and the proximal end tunneled under the skin to the location where the medical device 16 is to be implanted. Implantable medical device 16 is generally implanted subcutaneously at depths, depending upon application and device 16, of from 1 centimeter (0.4 inches) to 2.5 centimeters (1 inch) where there is sufficient tissue to support the implanted system. Once medical device 16 is implanted into the patient 18, the incision can be sutured closed and medical device 16 can begin operation.

Implantable medical device 16 operates to infuse a therapeutic substance into patient 18. Implantable medical device 16 can be used for a wide variety of therapies such as pain, spasticity, cancer, and many other medical conditions.

The therapeutic substance contained in implantable medical device 16 is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

Implantable medical device 16 can be any of a number of medical devices such as an implantable therapeutic substance delivery device, implantable drug pump, cardiac pacemaker, cardioverter or defibrillator, as examples.

Figure 2:
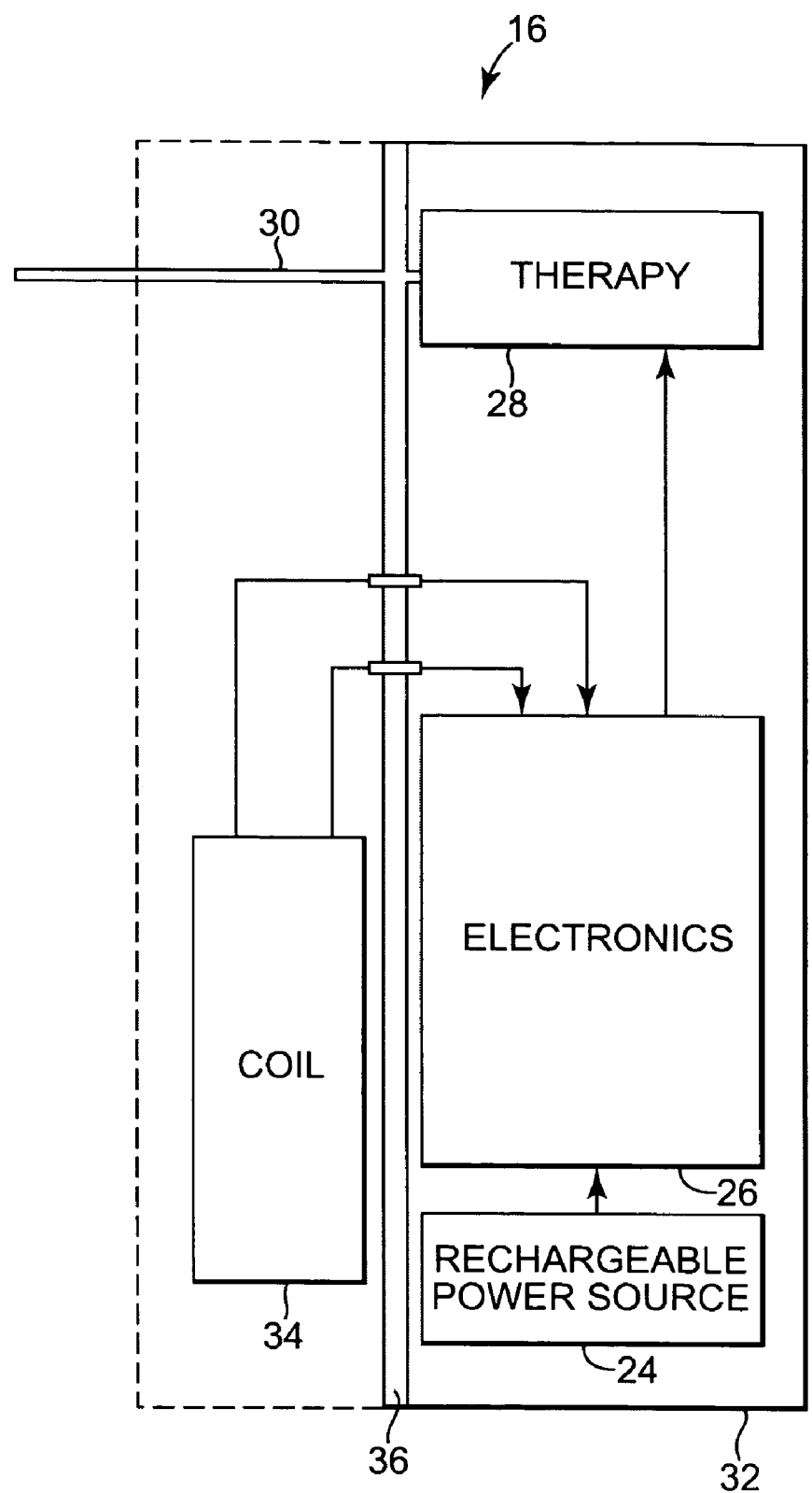
FIG. 2 is a block diagram of an implantable medical device.

In FIG. 2, implantable medical device 16 has a rechargeable power source 24, such as a Lithium ion battery, powering electronics 26 and therapy module 28 in a conventional manner. Therapy module 28 is coupled to patient 18 through one or more therapy connections 30, also conventionally. Rechargeable power source 24, electronics 26 and therapy module 28 are contained in hermetically sealed housing 32. Secondary charging coil 34 is attached to the exterior of housing 32. Secondary charging coil 34 is operatively coupled through electronics 26 to rechargeable power source 24. In an alternative embodiment, secondary charging coil 34 could be contained in housing 32 or could be contained in a separate housing umbilically connected to electronics 26. Electronics 26 help provide control of the charging rate of rechargeable power source 24 in a conventional manner. Magnetic shield 36 is positioned between secondary charging coil 34 and housing 32 in order to protect rechargeable power source 24, electronics 26 and therapy module 28 from electromagnetic energy when secondary charging coil 34 is utilized to charge rechargeable power source 24.

Rechargeable power source 24 can be any of a variety power sources including a chemically based battery or a capacitor. In a preferred embodiment, rechargeable power source is a well known lithium ion battery.

Figure 3:
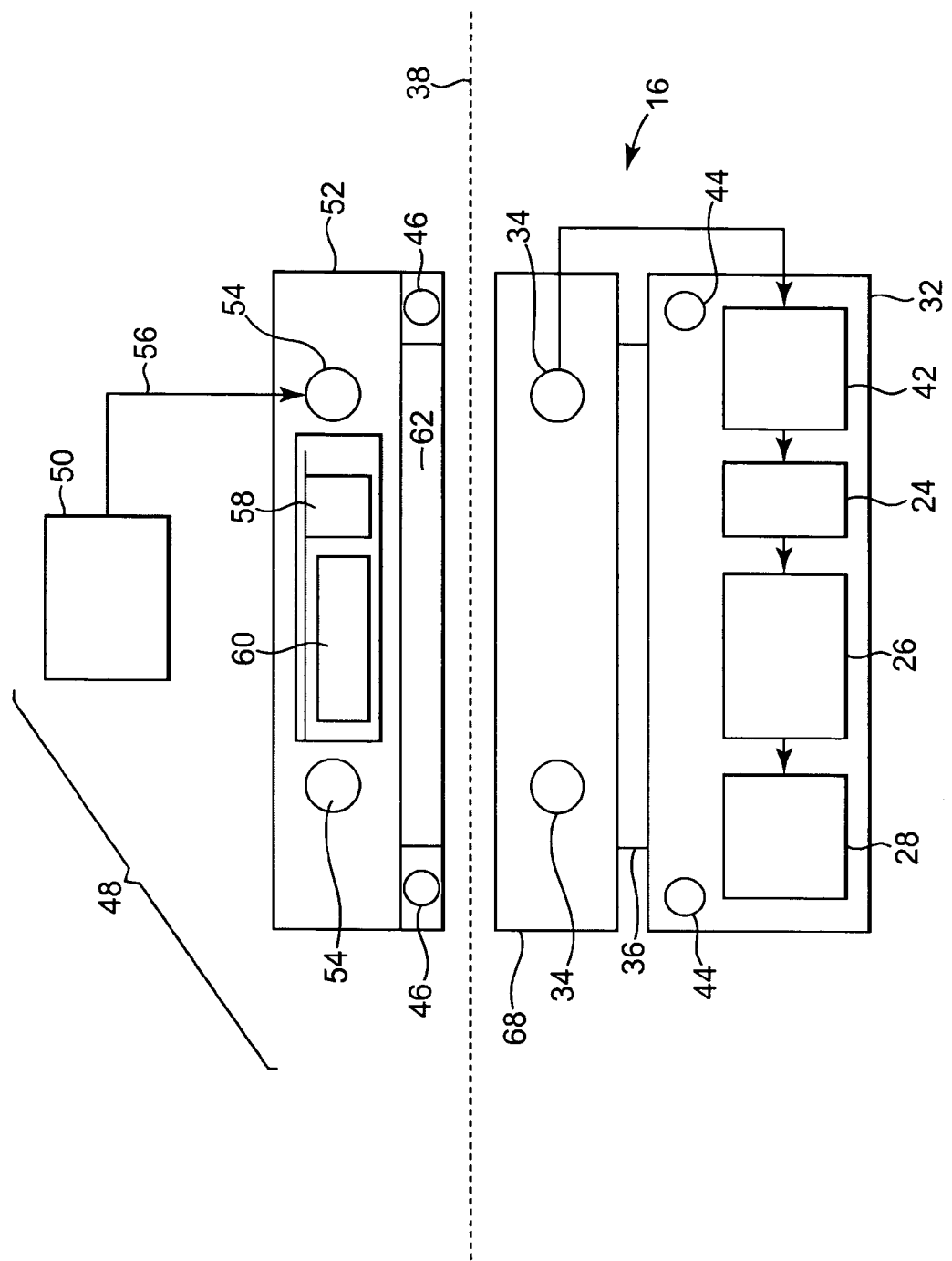
FIG. 3 is a detailed block diagram of an implantable medical device implanted sub-cutaneously and an associated external charging device in accordance with an embodiment of the present invention.

FIG. 3 illustrates an alternative embodiment of implantable medical device 16 situated under cutaneous boundary 38. Implantable medical device 16 is similar to the embodiment illustrated in FIG. 2. However, charging regulation module 42 is shown separate from electronics 26 controlling therapy module 28. Again, charging regulation and therapy control is conventional. Implantable medical device 16 also has internal telemetry coil 44 configured in conventional manner to communicate through external telemetry coil 46 to an external programming device (not shown), charging unit 50 or other device in a conventional manner in order to both program and control implantable medical device and to externally obtain information from implantable medical device 16 once implantable medical device has been implanted. Internal telemetry coil 44, rectangular in shape with dimensions of 1.85 inches (4.7 centimeters) by 1.89 inches (4.8 centimeters) constructed from 150 turns of 43 AWG wire, is sized to be larger than the diameter of secondary charging coil 34. Secondary coil 34 is constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Magnetic shield 36 is positioned between secondary charging coil 34 and housing 32 and sized to cover the footprint of secondary charging coil 34.

Internal telemetry coil 44, having a larger diameter than secondary coil 34, is not completely covered by magnetic shield 36 allowing implantable medical device 16 to communicate with the external programming device with internal telemetry coil 44 in spite of the presence of magnetic shield 36.

Rechargeable power source 24 can be charged while implantable medical device 16 is in place in a patient through the use of external charging device 48. In a preferred embodiment, external charging device 48 consists of charging unit 50 and external antenna 52. Charging unit 50 contains the electronics necessary to drive primary coil 54 with an oscillating current in order to induce current in secondary coil 34 when primary coil 54 is placed in the proximity of secondary coil 34. Charging unit 50 is operatively coupled to primary coil by cable 56. In an alternative embodiment, charging unit 50 and antenna 52 may be combined into a single unit. Antenna 52 may also optionally contain external telemetry coil 46 which may be operatively coupled to charging unit 50 if it is desired to communicate to or from implantable medical device 16 with external charging device 48. Alternatively, antenna 52 may optionally contain external telemetry coil 46 which can be operatively coupled to an external programming device, either individually or together with external charging unit 48.

As will be explained in more detail below, repositionable magnetic core 58 can help to focus electromagnetic energy from primary coil 46 to more closely be aligned with secondary coil 34. Also as will be explained in more detail below, energy absorptive material 60 can help to absorb heat build-up in external antenna 52 which will also help allow for a lower temperature in implantable medical device 16 and/or help lower recharge times. Also as will be explained in more detail below, thermally conductive material 62 is positioned covering at least a portion of the surface of external antenna 52 which contacts cutaneous boundary 38 of patient 18.

Figure 4:
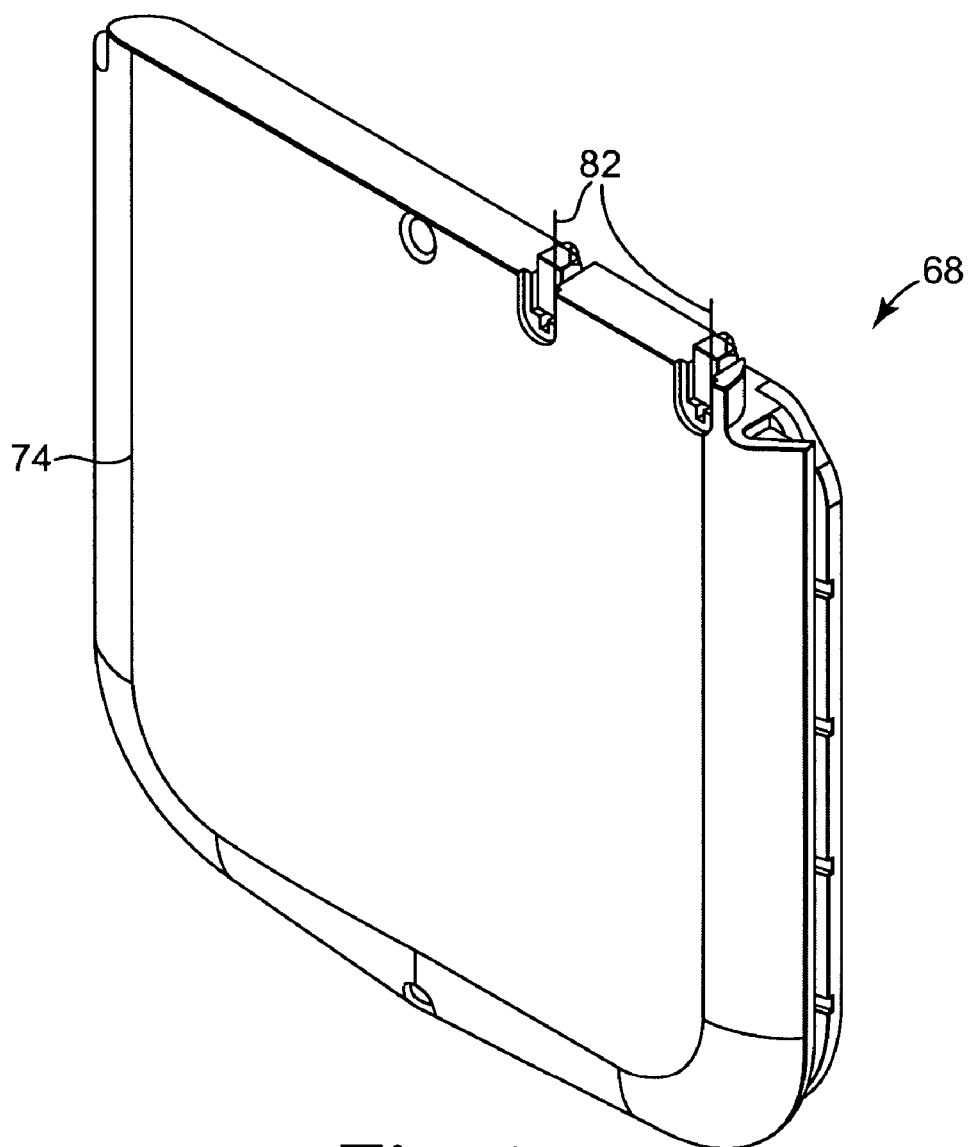
FIG. 4 is a perspective view of an internal antenna associated with an implantable medical device.
Figure 5:
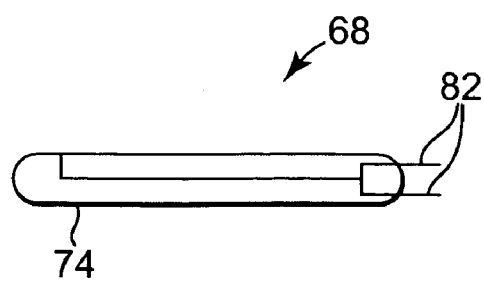
FIG. 5 is a side view of the internal antenna of FIG. 4.

In a preferred embodiment of internal antenna 68 as shown in FIG. 4 and FIG. 5, secondary coil 34 and magnetic shield 36 are separate from but adjacent to housing 32 encompassing the remainder of implantable medical device 16. Internal antenna 68 is contained in a separate housing 74 which is attachable to housing 32 so that implantable medical device 16 can be implanted by a medical professional as essentially one unit. Secondary coil 34 is electrically attached to charging regulation module 42 through leads 82.

In order to achieve efficient inductive coupling between primary coil 54 of external antenna 52 and secondary coil 34, it is desirable to place primary coil 54 of external antenna 52 as close to secondary coil 34 as possible. Typically, external antenna 52 is placed directly on cutaneous boundary 38 and, since the location of implantable medical device 16 is fixed, the distance across cutaneous boundary 38 between primary coil 54 and secondary coil 34 is minimized as long as external antenna 52 is kept adjacent cutaneous boundary 38.

Figure 6:
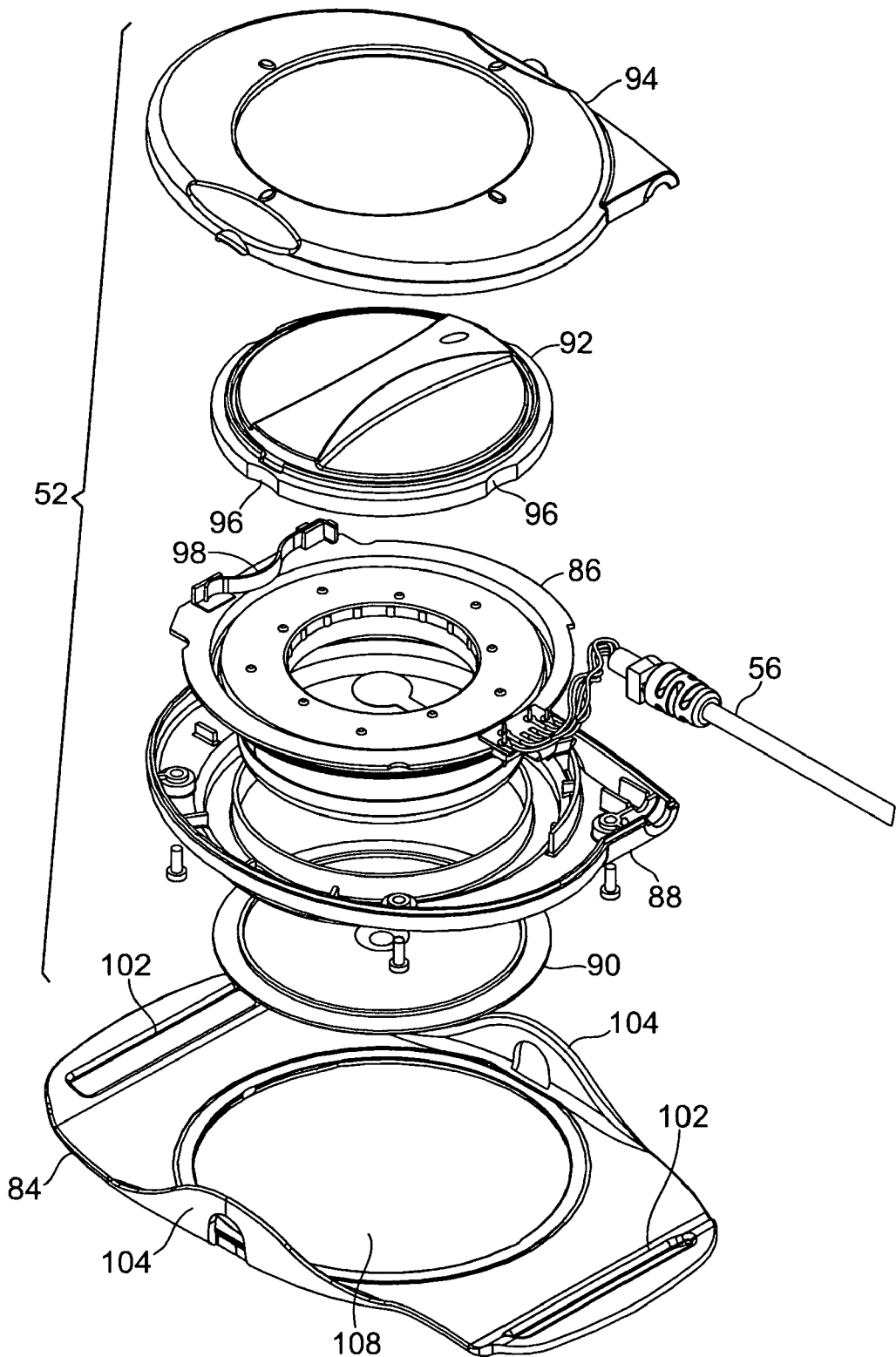
FIG. 6 is an exploded perspective view an external antenna and associated bracket in accordance with an embodiment of the present invention.

In a preferred embodiment, external antenna 52 is attachable to patient 18 with bracket 84 when charging rechargeable power source 24. FIG. 6 is an exploded illustration of a preferred embodiment of external antenna 52 attachable to bracket 84. Primary coil 54 is contained in bobbin assembly 86 which sits in bottom housing 88. Primary coil is connectable to cable 56. The bottom of external antenna 52 is formed from a thermally conductive material 90. Rotating core cup assembly 92 is held in place by top housing 94. Rotating core cup assembly 92 is rotatable is allowed to rotate within external antenna 52. Detents 96 engage detent spring 98 to position rotatable core cup assembly 92 in one of a plurality of detent positions. External antenna may be secured together, for example, with screws (not shown) holding top housing 94 and thermally conductive material 90 together.

Bracket 84 is adapted to be attached to the body of patient 18 with a belt (not shown) attachable to bracket 84 with belt loops 102. Ears 104 are adapted to mate with tabs 106 in top housing 94 and pivotally secure external antenna 52 in bracket 84 when charging is to be accomplished. Bracket 84 has an opening 108 allowing thermally conductive material 90 of external antenna 52 to contact the skin of patient 18 when external antenna 52 is pivotally secured in bracket 84.

As bracket 84 is attached to patient 18 with a belt via belt loops 102, the skin surface of patient 18 is typically not completely flat. For example, if implantable medical device 16 is implantable in the body torso of patient 18, then the belt attached via belt loops 102 will typically pass around the torso of patient 18. Since the torso of patient 18, and especially the torso of patient 18 near the location of implantable medical device 16, bracket 84 may not sit completely flat on patient 18. This may be especially true as patient 18 moves and the torso flexes during such movement. It is preferred that bracket 84 be conformal and flexible in order to conform to the shape of the body of patient 18. However, it is also preferred that bracket 84 be rigid enough so that opening 108 in bracket 84 maintain it shape in order to properly receive external antenna 52. Bracket 84 is preferably constructed of PCABS. To maintain the proper position of bracket 84 with the skin of patient 18, the surface of bracket 84 closest to patient 18 contains material 109 constructed from a high durometer, e.g., 40 Shore A, or "sticky" material such as a material known under the tradename of "Versaflex" manufactured by GLS Corp. of McHenry, Ill. This will help external antenna to sit more closely to the skin surface of patient 18 and remain there during movements of patient 18 throughout the charge or recharge cycle. In addition, external antenna 52 is allowed to pivot by way of ears 104 on tabs 106. Bracket 84 is configured to allow thermally conductive material 90 to extend through opening 108 and contact the skin surface of patient 18. Allowed pivoting of external antenna 52 and, hence, thermally conductive material 90, permits thermally conductive surface to sit more closely to the skin surface of patient 18.

Figure 7:
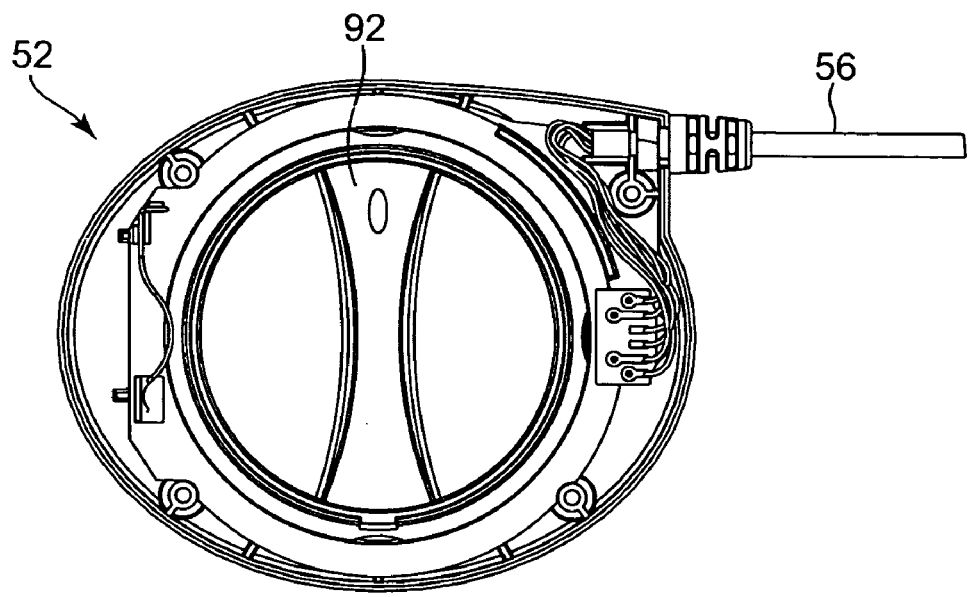
FIG. 7 is a top view of an external antenna in accordance with an embodiment of the present invention.

FIG. 7 is a partially cut away top view of external antenna 52 is assembled form and attached to cable 56. Rotatable core cup assembly 92 is shown located inside of primary coil 54 and positionable in selected rotated positions via detents 96 and detent spring 98. In FIG. 7, rotatable core cup assembly is positioned between with detent spring 98 between detents 96 illustrating that while multiple detent positions are available, rotatable core cup assembly can be positioned between detent positions and, indeed, at any rotated position.

Figure 8:
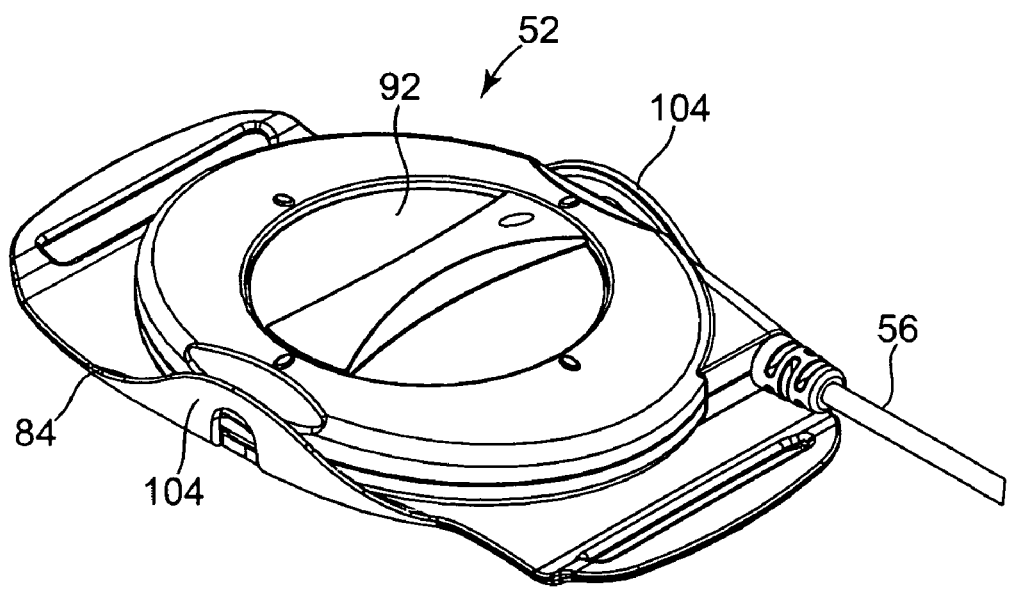
FIG. 8 is a perspective view of an external antenna and bracket combination in accordance with an embodiment of the present invention.

In FIG. 8, the assembly of external antenna 52 with bracket 84 is shown connected to cable 56. It is preferred that bracket 84 be affixed to patient 18 through belt loops 102 and then, after bracket 84 has been affixed to patient 18, external antenna 52 be attached to bracket 84. Affixing bracket 84 to patient 18 first allows for bracket 84 to be used to laterally position external antenna close to the position of implantable medical device 16.

Typical prior art positioning systems rely on the external antenna for lateral positioning. The external antenna is moved around on the body of the patient 18 until the best lateral position is found. When the best lateral position is found, the external antenna is removed from the body and the bottom of the external antenna (the portion of the external antenna) contacting the patient's body) is made to be resistant to lateral movement. As an example, one way is to remove a protective liner exposing a sticky surface allowing the external antenna to be relatively fixed in location. However, the very act of lifting the external antenna in order to remove the protective liner and replacing the external antenna on the body of the patient 18 causes crucial positioning information to be lost. There is no guarantee, and in fact it is not likely, that the external antenna will be replaced in the exact same position as the position previously found to be best.

In contrast, bracket 84 of the present invention can be used to roughly find the optimum position for external antenna 52. This can be done relatively easily due to opening 108 in bracket 84. Implantable medical device 16, when implanted, usually leaves an area of the body of patient 18 which is not quite as flat as it was before implantation. That is, implantable medical device 16 usually leaves an area of the skin of patient 18 which bulges somewhat to accommodate the bulk of implantable medical device 16. It is relatively easy for patient, medical professional or other person, to place bracket 84 in the general area of implantable medical device 16 and move bracket 84 around until the bulge caused by implantable medical device 16 is most closely centered in opening 108. As bracket 84 is moved laterally, opening 108 tends to naturally center on the bulge created by implantable medical device 16. Once positioned in this manner, bracket 84 can be secured to the body of patient 18 with belt (not shown) attached via belt loops 102. Securing and/or tightening, by pulling the belt tight or snapping a buckle, for example, can be without removing bracket 84 from the body of patient 16. Thus, bracket 84 can be relatively easily positioned over the general location of implantable medical device 16 and secured in that position without be removed from the body of patient 18.

Figure 9:
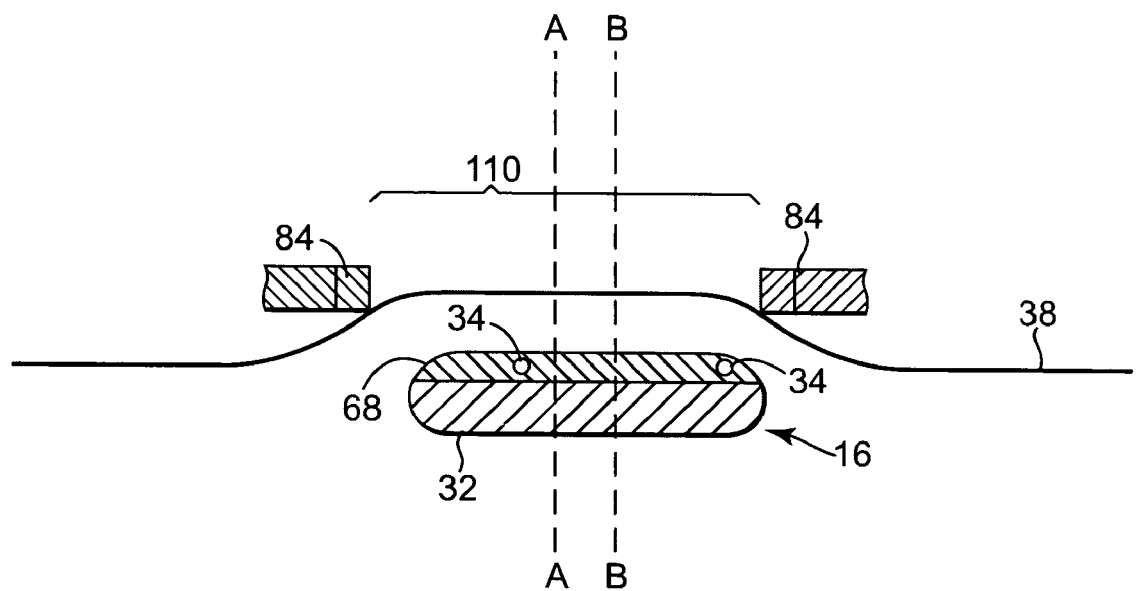
FIG. 9 is a cross-sectional side view of an implantable medical device implanted sub-cutaneously and an associated bracket for use with an external antenna.

FIG. 9 is cross-sectional view of implantable medical device 16 implanted in patient 18 approximately one centimeter under cutaneous boundary 38 creating bulging area 110, an area of the body of patient 18 in which the skin of patient 18 is caused to bulge slightly due to the implantation of implantable medical device 16. Bulging area 110 is an aid to locating the position of external antenna 52 relative to secondary coil 34. Bracket 84 can be positioned roughly in the area where implantable medical device 16 is implanted. Opening 108 in bracket 84 can aid is establishing the location of implantable medical device. Bracket 84 can be roughly centered over bulging area 110. After external antenna 52 is coupled to bracket 84, then primary coil 54 can be generally centered on implantable medical device 16.

However, secondary coil 34 may not be centered with respect to implantable medical device 16. This can occur due to a variety of reasons such as the need for operatively coupling secondary coil 34 to charging regulation module 42. Connections to make this operative coupling may require physical space on one side of internal antenna 68 which may cause secondary coil 34 not to be centered on implantable medical device 16. It is also possible that the attachment of internal antenna 68 to housing 32 can cause secondary coil 34 not to be centered on implantable medical device 16. Regardless of the cause, if secondary coil 34 is not centered on implantable medical device 16, then centering bracket 84 on bulging area 110 may not optimally position primary coil 54 with respect to secondary coil 34. Any offset in the position of primary coil 54 and secondary coil 34 may not result in the most efficient energy transfer from external antenna 52 to implantable medical device 16.

Figure 10:
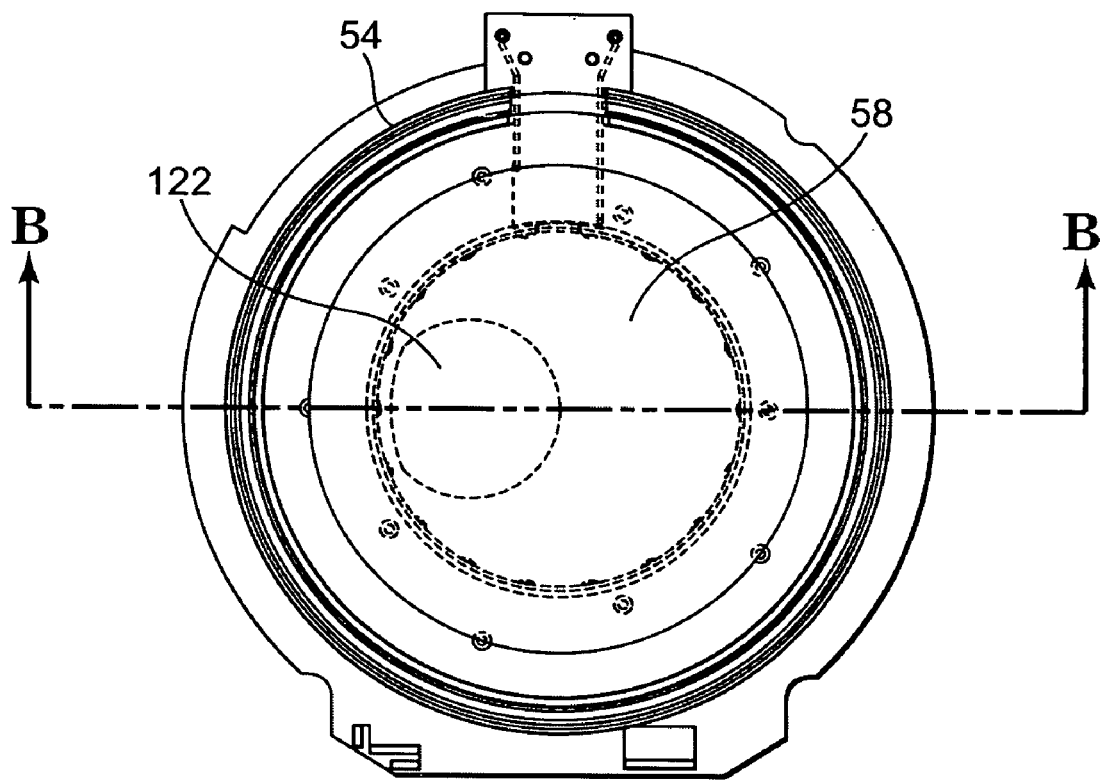
FIG. 10 is a cut-away top view of view a primary coil and associated magnetic core in accordance with an embodiment of the present invention.
Figure 11:
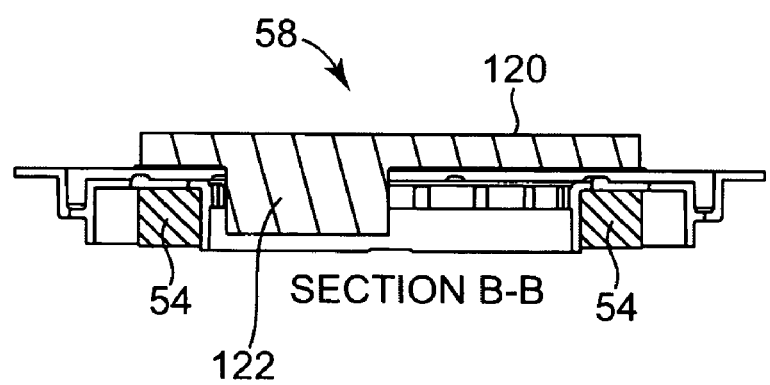
FIG. 11 is a cross-sectional view of the primary coil and associated magnetic core of FIG. 10 taken through section line B—B.

A magnetic core 58 is positioned within primary coil 54 in order to focus energy generated by primary coil 54. Magnetic core 58 attracts the magnetic flux lines generated by primary coil 54. The position of magnetic core 58 within primary coil 54 the lateral location of the largest amount of the flux lines generated by primary coil 54. FIGS. 10 and 11 show cut-away top and cross-sectional views of magnetic core 58 used with primary coil 54. Magnetic core 58 is moveable within primary coil 54. Lower portion 122 of magnetic core 58 can be rotated to a plurality of positions within primary coil 58 by rotating core cup assembly 92 (see FIG. 12). In a preferred embodiment, the travel path of magnetic core 58 can be locked in a plurality of discrete positions. In a preferred embodiment, magnetic core 58 is locked in four (4) different positions by detents 96 and detent spring 98 (see FIG. 6). Magnetic core 58 has an upper planar portion 120 and a smaller lower portion 122.

As magnetic core 58 is repositioned within primary coil 54, the focus of magnetic flux generated by primary coil 54 is also repositioned. As noted above, external antenna 52 is generally aligned with implanted medical device 16 using palpatory sensation. Moveable magnetic core 58 can then be used to provide a "fine" adjustment to the lateral positioning of external antenna 52 with respect to secondary coil 34. After bracket 84 has been secured to patient 18, external antenna 52 is attached to bracket 84. Magnetic core 58 is then moved until the best lateral alignment with secondary coil 34.

Figure 12:
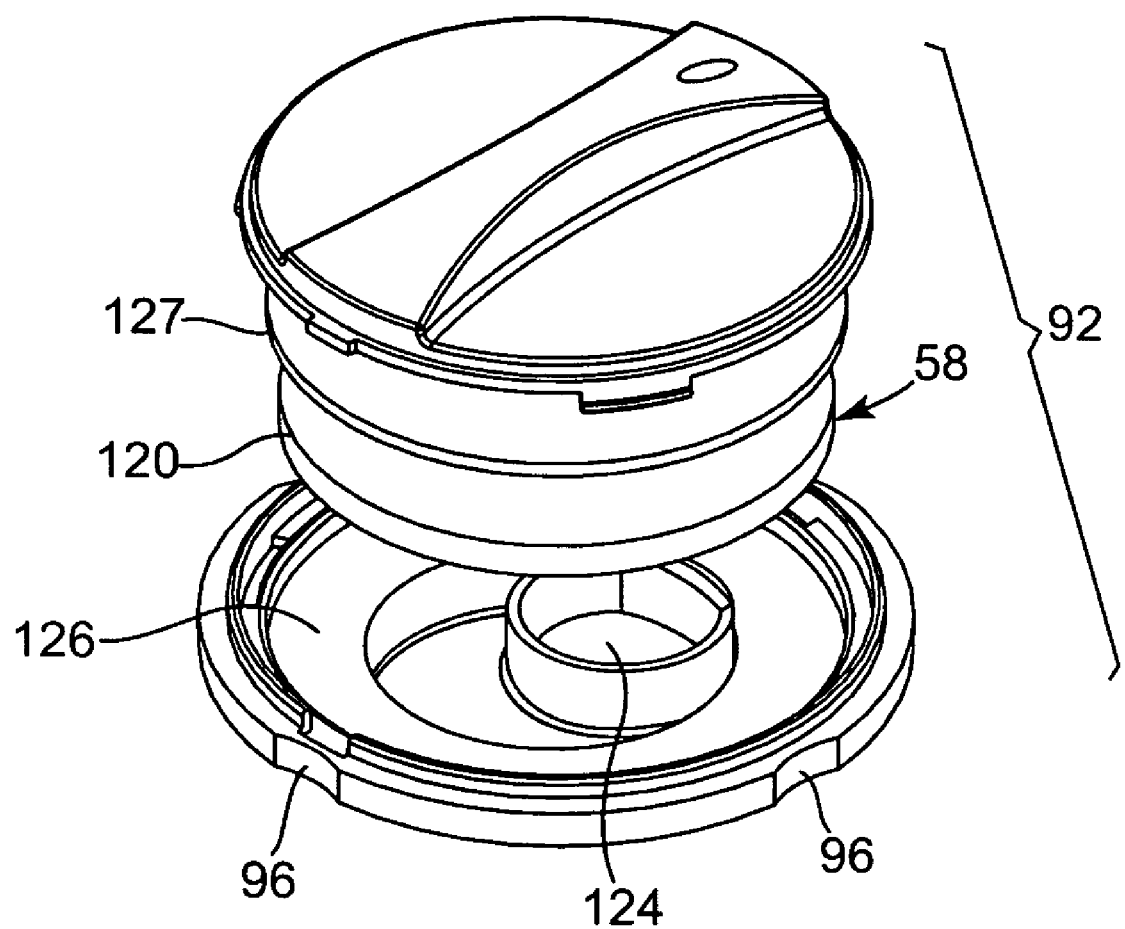
FIG. 12 is an exploded view a portion of an external antenna constructed in accordance with an embodiment of the present invention showing the magnetic core and a core cup assembly.

Magnetic core 58 is shown positioned within external antenna 52 of FIG. 12. Core cup assembly 92 holds magnetic core 58 within the assembly of external antenna 52. Lower portion 122 (not visible in FIG. 12) of magnetic core 58 fits into recess 124 of core cup assembly 92 while upper portion 120 of magnetic core 58 rests upon ledge 126 of core cup assembly 92. Preferably, magnetic core 58 is a ferrite core. Still more preferably, magnetic core 58 is constructed from MN60LL high performance, low loss ferrite manufactured by Ceramic Magnetics, Inc., Fairfield, N.J. Magnetic core 58 has an initial permeability of 6,500 and a maximum permeability of 10,500 (typical) with a volume resistivity of 500 ohm-centimeters.

A surface, preferably the top, of magnetic core 58 is lined with an adhesive coated foam 127 and contained in core cup assembly 92. Magnetic core 58 has a tendency to be brittle. Containing magnetic core 58 is core cup assembly assures that even if magnetic core 58 has one or more fractures, magnetic core 58 will still be properly positioned and continue to function. Foam 127 also helps to hold magnetic core 58 together and minimize gaps between fractured segments of magnetic core 58. Further, foam 127 adds mechanical stability to magnetic core 58 helping to cushion magnetic core 58 against mechanical impacts, such as from dropping external antenna 52 against a hard surface, and helps to prevents audible rattles which may otherwise develop from a fractured magnetic core 58.

Figure 13:
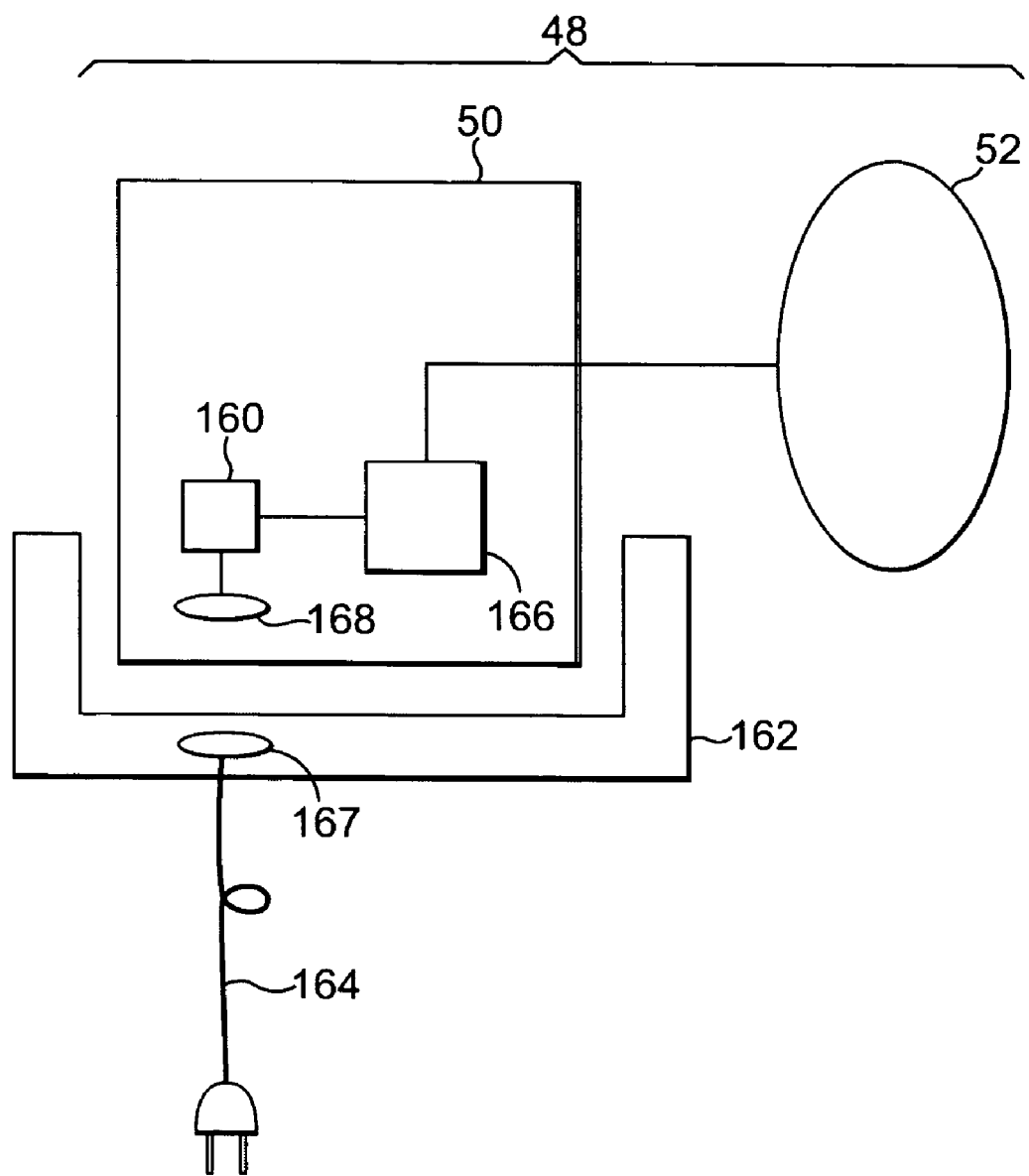
FIG. 13 is block diagram of an external charging unit and an associated inductively coupled cradle for recharging the external charging unit.

As shown in FIG. 13, external charging device 48 can be powered either directly from internal (to charging unit 50) batteries 160 or indirectly from desktop charging device 162. Desktop charging device is connectable via power cord 164 to a source of AC power, such as a standard readily available wall outlet. Desktop charging device 162 can be configured as a cradle which can receive charging unit 50. Other forms of connection from desktop charging device 162 to a power source, such as by a dedicated line cable can also be utilized. Desktop charging device 162 can charge and/or recharge batteries 160 in charging unit 50, preferably by inductive coupling using coil 167 positioned in desktop charging device 162 and coil 168 positioned within charging unit 50. Once charged and/or recharged, batteries 160 can provide the power through internal circuitry 168 and cable 56 to external antenna 52. Since charging unit 50 is not, in a preferred embodiment, coupled directly to the line voltage source of AC power, charging unit 50 may be used with external antenna 52 to transfer power and/or charge implanted medical device 16 while desktop charging device 162 is coupled to a line voltage source of AC power. The inductive coupling using coil 167 and coil 168 break the possibility of a direct connection between the line voltage source of AC power and external antenna 52. Batteries 160 also allow charging unit 50 and, hence, external charging device 48, to be used in transferring power and/or charging of implanted medical device 16 while completely disconnected from either a line voltage source of AC power or desktop charging device 162. This, at least in part, allows patient 18 to be ambulatory while transferring power and/or charging implanted medical device 16.

Figure 14:
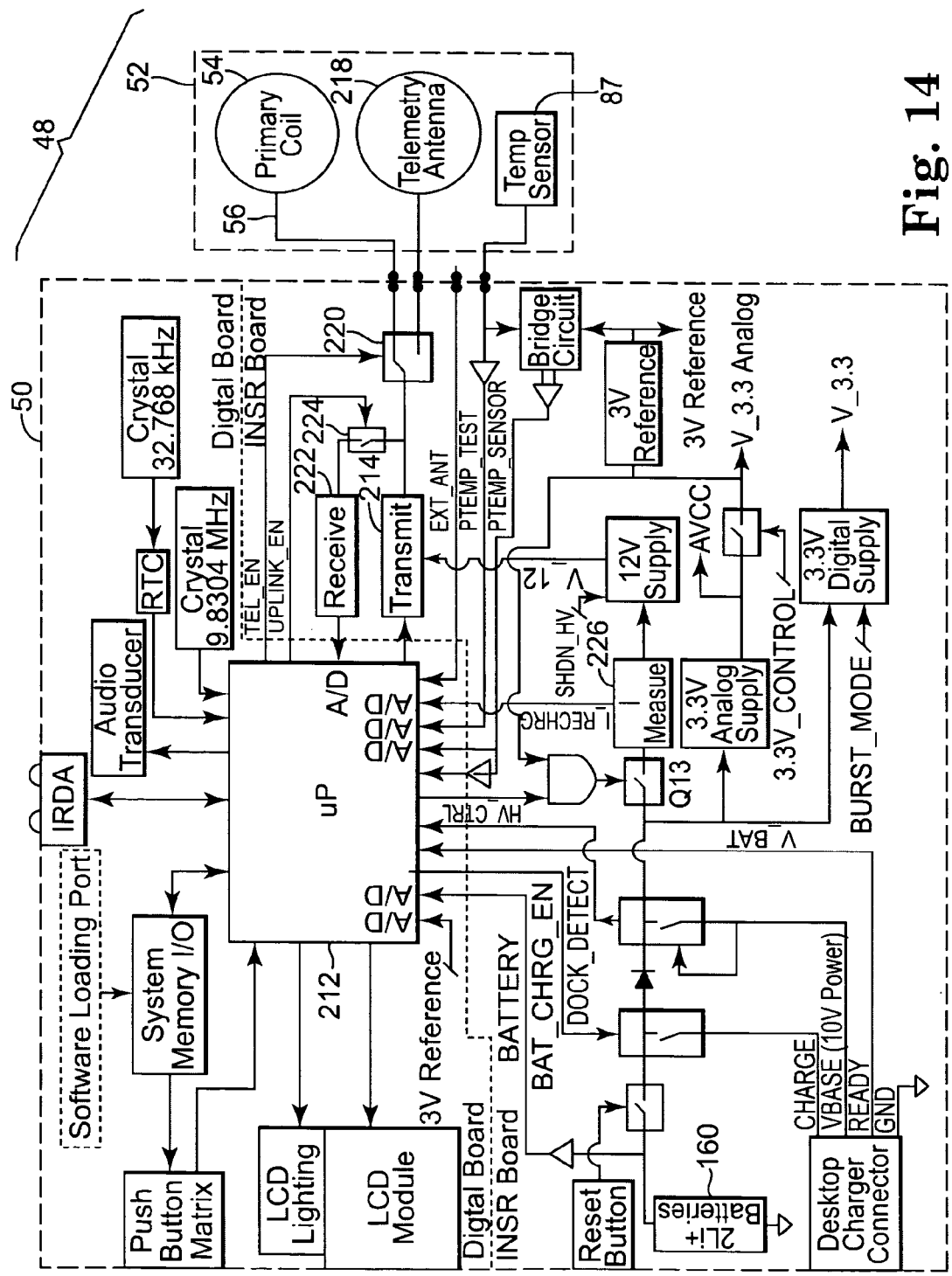
FIG. 14 is a detailed block diagram of the external charging unit of FIG. 13.

FIG. 14 is a block diagram of external charging device 48 controlled by microprocessor 212. Transmit block 214 consists of an H-bridge circuit powered from 12 volt power supply 216. Transmit block 214 drives primary coil 54 in external antenna 52. H-bridge control signals and timing are provided conventionally by microprocessor 212. H-bridge circuit in transmit block 214 is used to drive both primary coil 54, used for power transfer and/or charging, and telemetry antenna 218. Drive selection is done by electronically controllable switch 220. During power transfer and/or charging, H-bridge circuit is driven at 9 kiloHertz. During telemetry, H-bridge circuit is driven at 175 kiloHertz.

Receive block 222 is used only during telemetry, enabled by switch 224, to receive uplink signals from implanted medical device 16. Twelve volt power supply 216 is a switching regulator supplying power to transmit block 214 during power transfer and/or charging as well as telemetry downlink. Nominal input voltage to 12 volt power supply 216 is either 7.5 volts from lithium ion batteries 226 or 10 volts from desktop charging device 162 (FIG. 13).

Current measure block 226 measures current to 12 volt power supply 216. Current measured by current measure block 226 is used in the calculation of power in along with the voltage of batteries 160. As noted above, power in is used in the calculation of efficiency of power transfer and/or charging efficiency to determine, in part, the best location of external antenna 52 and/or rotating core cup assembly 92.

Rotating core cup assembly 92 is rotated in external antenna 52 for better lateral alignment of primary coil 54 and secondary coil 34. A feedback mechanism is used to determine the best rotation of core cup assembly 92. External charging device 48 can determine whether the current position of rotating core cup assembly 92 is optimally aligned for energy transfer and/or charging. External charging device 48 measures the power out of external charging device 48 divided by the power into external charging device 48. This calculation is a measure of the efficiency of external charging device 48. The power out is gauged by the power induced in implantable medical device 16 and is determined by multiplying the voltage of rechargeable power source 24 by the charging current in implantable medical device 16. These values are obtained by telemetry from implanted medical device 16. The power in is gauged by the power generated by charging unit 50 and is determined by multiplying the voltage of the internal voltage of charging unit 50, e.g., the voltage of a battery or batteries internal to charging unit 50, by the current driving external antenna 52.

The ratio of power out divided by power in can be scaled displayed to patient 18, or a medical professional or other person adjusting rotatable core cup assembly 92 or positioning external antenna 52. For example, the available efficiency can be divided into separate ranges and displayed as a bar or as a series of lights. The separate ranges can be linearly divided or can be logarithmic, for example.

Using efficiency as a measure of effective coupling and, hence, as a measure of proper location of external antenna 52 and rotatable core cup assembly 92 works not only at high charging or power transfer levels but also at reduced charging levels, as for example, when charging at reduced levels toward the end or beginning of a charging cycle.

If, after patient 18 or other person has moved rotatable core cup assembly 92 through all of the range of positions on external antenna 52 and can not achieve an acceptable efficiency level, patient 18 or other person can remove external antenna 52 from bracket 84, realign bracket 84 with bulging area 110, reattach external antenna 52 to bracket 84 and restart the alignment and coupling efficiency process.

Figure 15:
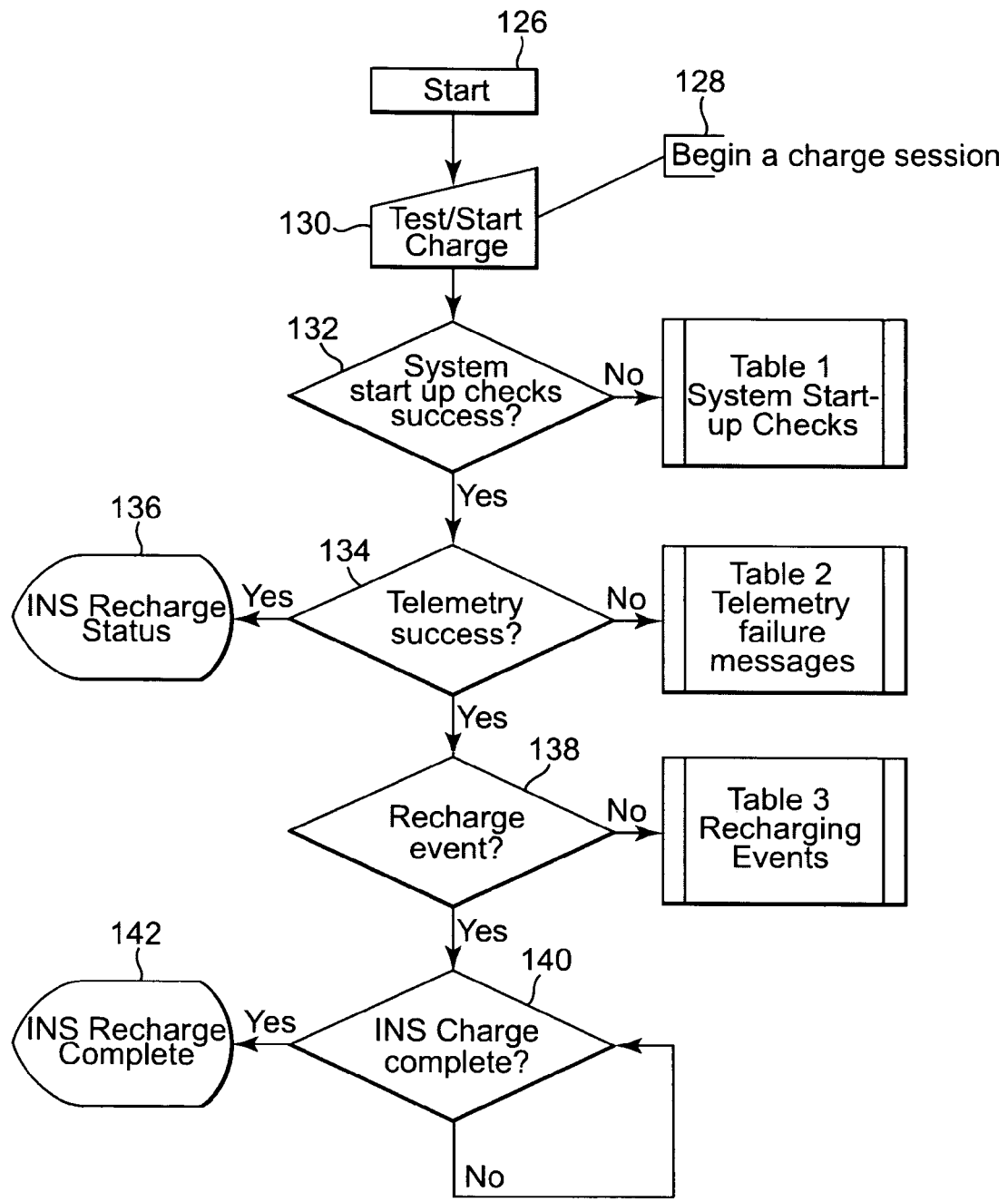
FIG. 15 is a flow chart illustrating a charging process in accordance with an embodiment of the present invention.

FIG. 15 is a flow chart illustrating an exemplary charging process using external antenna 52. The process starts [block 126] and a charging session begins [block 128] with a test [block 130]. The charging system performs start-up checks [block 132]. If the start-up checks are not performed successfully, the actions taken in Table 1 are performed.

TABLE 1

| Check | Screen/Message |
|---|---|
| System Errors: e.g., stuck key | System Error |
| External Charger Battery Status | Recharge Complete |
|  | Battery Low |
|  | Recharge External Charger |
| External Charger Connected to External Antenna | Recharge in Process Icon |
| Antenna Disconnect | Connect Antenna |

If the start-up checks are successful, telemetry with implantable medical device 16 is checked [block 134]. If telemetry is successful, the error messages indicated in Table 2 are generated.

TABLE 2

| Failure | Screen/Message |
|---|---|
| Poor Communication | Reposition Antenna |
| External Charger Error Code Response | Call Manufacturer |
| Communication Error | Communication Error |
| External Charger Fault | Call Manufacturer |
| Antenna Disconnect | Connect Antenna |
| Antenna Failure | Antenna Failure Icon |

If telemetry checks are successful, external charging device 48 is able to monitor [block 136] charging status. Monitoring charging status can includes providing feedback to an operator to help determine the best rotational position of core cup assembly 92.

Charge events are checked [block 138]. If no charge events are noted, the actions indicated in Table 3 are executed.

TABLE 3

| Event | Screen/Message |
|---|---|
| Telemetry Failure | (See Messages From Table 2) |
| Implantable Medical Device Battery Low | Device Battery Low |
| External Charger Battery Low | Charger Battery Low |
| External Charger Battery Depleted | Recharge Charger |
| External Charger Recharge Complete | External Charger Recharge Complete |
| Implantable Medical Device Will Not Provide Therapeutic Result Until Recharged: Therapy Unavailable/Sleep Mode | Recharge Device |
| Antenna Disconnect | Connect Antenna |

If a charge event occurs, then the process checks to determine if charging is complete [block 140]. Once charging is complete, the process terminates [block 142].

As energy is transferred from primary coil 54 of external antenna 52 to secondary coil 34 of implantable medical device 16, heat may also be generated in implantable medical device 16 in surrounding tissue of patient 18. Such heat build-up in tissue of patient 18, beyond certain limits, is undesirable and should be limited as acceptable values. Generally, it is preferable to limit the temperature of external antenna 52 to not more than forty-one degrees Centigrade (41° C.) and to limit the temperature of implanted medical device 16 and the skin of patient 18 to thirty-nine degrees Centigrade (39° C.). In order to ensure that implantable medical device 16 is less than the upper limit of thirty-nine degrees Centigrade (39° C.), it is preferred that the actual temperature of external antenna 52 be less than thirty-nine degrees Centigrade (39° C.). In general, the temperature of external antenna 52 should be maintained to be less than or equal to the desired maximum temperature of implanted medical device 16. While the temperature limits discussed above are preferred under current conditions and regulations, it is recognized and understood that conditions and regulations may change or be different in different circumstances. Accordingly, the actual temperatures and temperature limits may change. In a preferred embodiment, such temperature limits are under software control in charging unit 50 so that any such temperatures or temperature limits can be modified to fit the then current circumstances.

Magnetic shield 36 serves to at least partially protect the portion of implantable medical device 16 contained within titanium housing 32 from the effects of energy transfer from external charging device 48 produced through inductive coupling from primary coil 54. Magnetic shield 36 is constructed of Metglas magnetic alloy 2714A (cobalt-based) manufactured by Honeywell International, Conway, S.C. Magnetic shield 36 is positioned between secondary coil 34 and housing 32 of implantable medical device 16 with secondary coil 34 facing cutaneous boundary 38. Magnetic shield does not interfere with the operation of secondary coil 34 because magnetic shield 36 is positioned away from primary coil 54. Also, magnetic shield does not interfere with telemetry between implantable medical device 16 and an external programmer because magnetic shield 36 is smaller than internal telemetry coil 44. That is, internal telemetry coil 44 lies outside of magnetic shield 36.

However, the material of magnetic shield 36 substantially limits the electromagnetic energy induced by primary coil 54 from penetrating beyond magnetic shield. Electromagnetic waves induced by primary coil 54 that reach titanium housing 32 will tend to be absorbed by titanium housing 54 and its components and will tend to cause the temperature of titanium housing 54 to rise. As the temperature of titanium housing 54 rises, such temperature increase will be disadvantageously transferred to the surrounding tissue of patient 18. However, any electromagnetic waves which are prevented from reaching titanium housing 32 will not cause such a temperature rise.

Thermally conductive material 62 of external antenna 52 is positioned to contact the skin of patient 18 when external antenna 52 is placed for energy transfer, or charging, of implanted medical device 16. Thermally conductive material 62 tends to spread any heat generated at the skin surface and spread any such heat over a larger area. Thermally conductive material 62 tends to make the temperature of the skin surface more uniform than would otherwise be the case. Uniformity of temperature will tend to limit the maximum temperature of any particular spot on the skin surface. The skin itself is a pretty good conductor of heat and initially spreading any heat generated over a larger area of the skin will further assist the skin in dissipating any heat build-up on to surrounding tissue and further limit the maximum temperature of any particular location on the surface of the skin.

Thermally conductive material 62 is molded into the surface of external antenna 52 which will contact the skin surface of patient 18 when external antenna 52 provides energy transfer to implanted medical device 16. Since thermally conductive material 62 should pass electromagnetic energy from primary coil 54, thermally conductive material 62 should be constructed from a non-magnetic material. It is desirable that thermally conductive material 62 have a thermal conductivity of approximately 5.62 BTU inch/hour feet$^2$ degrees Fahrenheit (0.81 W/meters degrees Kelvin). In a preferred embodiment, thermally conductive material is constructed from a proprietary composite of approximately forty percent (40%) graphite, seven percent (7%) glass in RTP 19×103410 A polypropylene, manufactured by RTP Company, Winona, Minn. It is also preferable that thermally conductive material not be electrically conductive in order to reduce eddy currents. In a preferred embodiment, thermally conductive material has a volume resistivity of approximately $10^3$ ohm-centimeters and a surface resistivity of $10^5$ ohms per square.

Energy absorptive material 62 is placed in and/or around primary coil 54 of external antenna 52 in order to absorb some of the energy generated by primary coil 54. In a preferred embodiment, energy absorptive material 62 fills in otherwise empty space of rotating core cup assembly 92. Heat generated by energy produced by primary coil 54 which is not effectively inductively coupled to secondary coil 34 will tend to cause a temperature rise in other components of external antenna 52 and, possibly, the skin of patient 18. At least a portion of this temperature rise can be blocked through the use of energy absorptive material 62. Energy absorptive material 62 is chosen to absorb heat build-up in surrounding components and tend to limit further temperature increases. Preferably, energy absorptive material 62 is selected to be material which undergoes a state change at temperatures which are likely to be encountered as the temperature of surrounding components rises during energy transfer, e.g., charging, using external antenna 52.

If it is a goal to limit the temperature of the skin of patient 18 to thirty-nine degrees Centigrade (39° C.), it is desirable to use of energy absorptive material 62 which has a state change at or near the temperature limit. In this example, the use of an energy absorptive material 62 having a state change in temperature area just below thirty-nine degrees Centigrade (39° C.), preferably in the range of thirty-five degrees Centigrade (35° C.) to thirty-eight degrees Centigrade (38° C.), can help limit the rise in the temperature of the skin of patient 18 to no more than the desired limit, in this example, thirty-nine degrees (39° C.).

As the temperature of surrounding components of external antenna 52 rise to a temperature which is just below the temperature at which energy absorptive material 62 changes state, at least a portion of further heat energy generated by primary coil 54 and surrounding components of external antenna 52 will go toward providing the energy necessary for energy absorptive material 62 to change state. As energy absorptive material 62 is in the process of changing state, its temperature is not increasing. Therefore, during the state change of energy absorptive material 62, energy absorptive material 62 is serving to at least partially limit a further rise in the temperature of components of external antenna 52. As the state change temperature of energy absorptive material has been preferably selected to be near or just below the temperature limit of the skin of patient 18, energy absorptive material 62 will tend to limit the temperature components of external antenna 52 from reaching the temperature limit and, hence, will also tend to limit the temperature of the skin of patient 18 from reaching the maximum desired temperature limit.

In a preferred embodiment, energy absorptive material 62 is constructed from wax and, in particular, a wax which has change of state temperature of approximately the maximum temperature at which external antenna 52 is desired to reach, such as thirty-eight (38) or thirty-nine (39) degrees Centigrade. Thus, it is preferred that the wax material of which energy absorptive material is constructed melt at that temperature.

Inductive coupling between primary coil 54 of external antenna 52 and secondary coil of implantable medical device 16 is accomplished at a drive, or carrier, frequency, $f_{carrier}$, in the range of from eight (8) to twelve (12) kiloHertz. In a preferred embodiment, the carrier frequency $f_{carrier}$, of external antenna 54 is approximately nine (9) kiloHertz unloaded.

However, the inductive coupling between primary coil 54 of external antenna 52 and secondary coil 34 of implantable medical device is dependent upon the mutual inductance between the devices. The mutual inductance depends upon a number of variables. Primary coil 54 is preferably made from a coil of wire that has an inductance L and a series or parallel tuned capacitance C. The values of both inductance L and capacitance C are fixed. For instance, if the desired drive frequency, $f_{carrier}$, of the energy transfer system was to be 1 megaHertz and external antenna 52 had an independence of one microHenry, capacitance would be added so that the resonant frequency of the energy transfer system would equal that of the drive frequency, $f_{carrier}$. The total capacitance added can be found using the equation $f_{resonate}$ equals one divided by two times pi ($\pi$) times the square root of L times C where L is the inductance of the energy transfer system. In this example, the value of capacitance C required to tune external antenna 52 to resonate at the carrier frequency of 1 megaHertz is calculated as approximately 25 nanofarads.

However, when the electrical properties of external antenna 52 change, either by the reflected environment or due to a physical distortion or change in the composition of the external antenna 52, the inductance, L, may be altered. The inductance, L, can be altered because it is made up of two separate parts. The first part is the self-inductance, $L_{self}$, of external antenna 52 at $f_{carrier}$. The second part is the mutual inductance, $L_{mutual}$, which is a measure of the change in current driving external antenna 52 and the magnetic effect, or "loading", which the environment has on external antenna 52. When the electrical characteristics of the environment of external antenna 52 change, $L_{self}$ remains constant while $L_{mutual}$ varies. The effect of a change in the overall inductance, whether that change is from $L_{self}$ or from $L_{mutual}$, is a change in the resonant frequency, $f_{resonate}$. Since C was chosen in order to have the resonant frequency, $f_{resonate}$, match the drive frequency, $f_{carrier}$, in order to increase the efficiency of energy transfer from primary coil 54 of external antenna 52 to secondary coil 34, a change in either or can result in the resonant frequency, $f_{resonate}$, being mismatched with the drive frequency, $f_{carrier}$. The result can be a less than optimum efficiency of energy transfer to implantable medical device 16.

As the drive frequency, $f_{carrier}$, varies with respect to the resonant frequency, $f_{resonate}$, apparent impedance of the energy transfer system, as seen by primary coil 54, will vary. The apparent impedance will be at a minimum when the drive frequency, $f_{carrier}$, exactly matches the resonant frequency, $f_{resonate}$. Any mismatch of the drive frequency, $f_{carrier}$, from the resonant frequency, will cause the impedance to increase. Maximum efficiency occurs when the drive frequency, $f_{carrier}$, matches the resonant frequency, $f_{resonate}$.

As the impedance of the energy transfer system varies, so does the current driving primary coil 54. As the impedance of the energy transfer system increases, the current driving primary coil 54 will decreases since the voltage being applied to primary coil 54 remains relatively constant. Similarly, the current driving primary coil 54 will increase as the impedance of the energy transfer system decreases. It can be seen then that point of maximum current driving primary coil 54 will be at a maximum when the impedance of the energy transfer system is at a minimum, when the resonant frequency, $f_{resonate}$, matches the drive frequency, $f_{carrier}$, and when maximum efficiency occurs.

The impedance of the energy transfer system can be monitored since the current driving primary coil 54 varies as a function of drive frequency, $f_{carrier}$. The drive frequency can be varied and the current driving primary coil can be measured to determine the point at which the impedance of the energy transfer system is at a minimum, the resonant frequency, $f_{resonate}$, matches the drive frequency, $f_{carrier}$, and when maximum efficiency occurs.

In a preferred embodiment, instead of holding the drive frequency, $f_{carrier}$, constant for a nominal resonant frequency, $f_{resonate}$, the drive frequency, $f_{carrier}$, is varied until the current driving primary coil 54 is at a maximum. This is not only the point at which the impedance of the energy transfer system is at a minimum but also the point at which maximum efficiency occurs.

Maximum efficiency is not as important in systems, such as telemetry systems, which are utilized in a static environment or for relatively short periods of time. In a static environment, the resonant frequency, $f_{resonate}$, may be relatively invariable. Further, efficiency in not terribly important when energy or information transfer occurs over a relatively short period of time.

However, transcutaneous energy transfer systems can be utilized over extended periods of time, either to power the implanted medical device 16 over an extended period of time or to charge a replenishable power supply within implanted medical device 16. Depending upon capacity of the replenishable power supply and the efficiency of energy transfer, charging unit 50 can be utilized for hours and typically can be used as patient 18 rests or over night as patient 18 sleeps. Further, over the extended period of time in which charging unit 50 is utilized, external antenna 52 is affixed to the body of patient 18. As patient 18 attempts to continue a normal routine, such as by making normal movement or by sleeping, during energy transfer, it is difficult to maintain external antenna 52 in a completely fixed position relative to secondary coil 34. Movement of external antenna 52 with respect to secondary coil 34 can result in a change in mutual inductance, $L_{mutual}$, a change in impedance and a change in the resonant frequency, $f_{resonate}$. Further, any change in spatial positioning of the energy transfer system with any external conductive object, any change in the characteristics of external antenna 52, such as by fractures in magnetic core 58, for example, a change in the charge level of rechargeable power source 24 of implantable medical device 16 or a change in the power level of charging unit 50, all can result in a change of mutual inductance, $L_{mutual}$.

In a preferred embodiment, drive frequency, $f_{carrier}$, is varied, not only initially during the commencement of energy transfer, e.g., charging, but also during energy transfer by varying the drive frequency, $f_{carrier}$, in order to match the drive frequency, with the resonant frequency, $f_{resonate}$, and, hence, maintaining a relatively high efficiency of energy transfer. As an example, drive frequency, $f_{carrier}$, can be constantly updated to seek resonant frequency, $f_{resonate}$, or drive frequency, $f_{carrier}$, can be periodically updated, perhaps every few minutes or every hour as desired. Such relatively high efficiency in energy transfer will reduce the amount of time charging unit 50 will need to be operated, for a given amount of energy transfer, e.g., a given amount of battery charge. A reduced energy transfer, or charging, time can result in a decrease in the amount of heating of implanted medical device 16 and surrounding tissue of patient 18.

In a preferred embodiment, external charging device 48 incorporates temperature sensor 87 in external antenna 52 and control circuitry in charging unit 50 which can ensure that external antenna 52 does not exceed acceptable temperatures, generally a maximum of thirty-eight degrees Centigrade (38° C.). Temperature sensor 87 in external antenna 52 can be used to determine the temperature of external antenna 52. Temperature sensor 87 can be positioned in close proximity to thermally conductive material 62 in order to obtain reasonably accurate information on the temperature of the external surface of external antenna 52 contacting patient 18. Preferably, temperature sensor 87 is affixed to thermally conductive material 62 with a thermally conductive adhesive. Thermally conductive material 62 smoothes out any temperatures differences which otherwise might occur on the surface of external antenna 52 contacting patient 18. Positioning temperature sensor 87 in the proximity or touching thermally conductive material 62 enables an accurate measurement of the contact temperature.

Control circuitry using the output from temperature sensor 87 can then limit the energy transfer process in order to limit the temperature which external antenna 52 imparts to patient 18. As temperature sensor 87 approaches or reaches preset limits, control circuitry can take appropriate action such as limiting the amount of energy transferred, e.g., by limiting the current driving primary coil 54, or limiting the time during which energy is transferred, e.g., by curtailing energy transfer or by switching energy transfer on and off to provide an energy transfer duty cycle of less than one hundred percent.

When the temperature sensed by the temperature sensor is well below preset temperature limits, it may be acceptable to report the temperature with relatively less precision. As an example, if the temperature sensed by temperature sensor 87 is more than two degrees Centigrade (2° C.) away from a preset limit of thirty-eight degrees Centigrade (38° C.), it may be acceptable to know the temperature with an accuracy of three degrees Centigrade (3° C.).

However, when the temperature of external antenna 52 approaches to within two degrees Centigrade (2° C.), it may be desirable to know the temperature with a much greater accuracy, for example, an accuracy of within one tenth of one degree Centigrade (0.1 ° C.).

It is generally difficult, however, to produce a temperature which has a high degree of accuracy over a very broad temperature range. While a temperature sensor can easily be produced to provide a resolution within one-tenth of one degree Centigrade (0.1° C.) over a relatively narrow range temperatures, it can be difficult to produce a temperature sensor providing such a resolution over a broad range of temperatures.

In a preferred embodiment, a dual range temperature sensor is utilized. This temperature sensor has a first, broad, less accurate range of measurement from thirty-one degrees Centigrade (31° C.) to forty degrees Centigrade (40° C.) having an accuracy within three degrees Centigrade (3° C.). Further, this temperature sensor has a second, narrow, more accurate range of measurement over four degrees Centigrade (4° C.), from thirty-six degrees Centigrade (36° C.) to forty degrees Centigrade (40° C.), having an accuracy within one-tenth of one degree Centigrade (0.1° C.).

Figure 16:
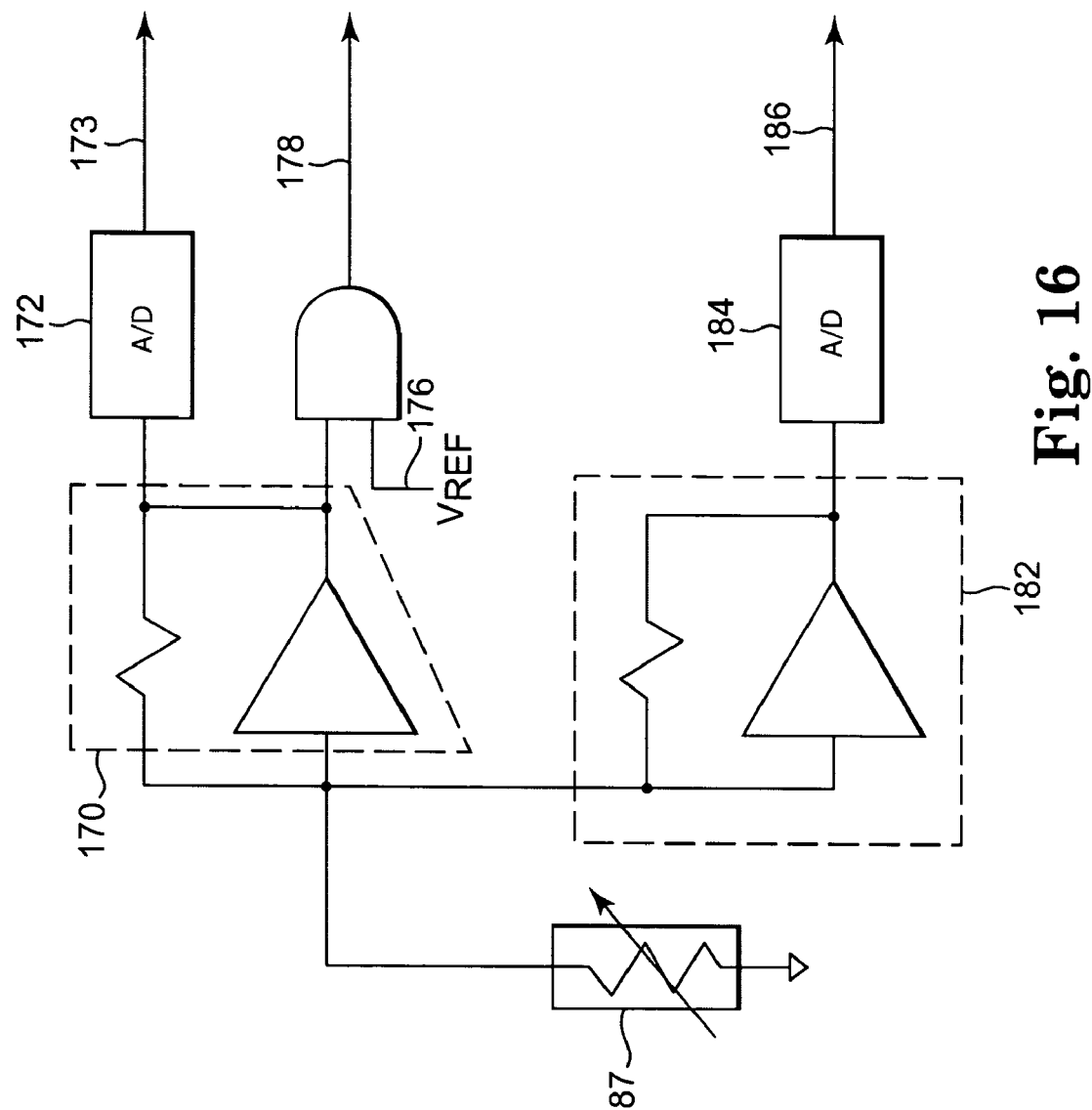
FIG. 16 is a schematic diagram of a dual range temperature sensor.

FIG. 16 illustrates a preferred embodiment of a dual range temperature sensor utilizing temperature sensor 87. Temperature sensor 87, located in external antenna 52, is coupled to amplifier 170 which has been pre-calibrated to operate only in the range of from thirty-six degrees Centigrade (36° C.) to forty degrees Centigrade (40° C.). Components of amplifier 170 have an accuracy reflecting a temperature within one-tenth of one degree Centigrade (0.1° C.). The analog output of amplifier 170 is sent to analog-to-digital converter 172 producing a digital output 173 having an accuracy of one-tenth of one degree Centigrade (0.1° C.). The analog output of amplifier 170 is also sent to comparator 174 which compares the analog output against a known reference voltage 176 which is set to at a predetermined level to produce a positive output 178 when temperature sensor 87 reflects a temperature of thirty-eight degrees Centigrade (38° C.), the maximum temperature permitted for external antenna 52. Control logic in charging unit 50 can then take appropriate action to limit further temperature increases such as by ceasing or limiting further energy transfer and/or charging. Temperature sensor 87 is also coupled to amplifier 182. Components of amplifier 182 have an accuracy reflecting a temperature within three degrees Centigrade (3° C.), much less accuracy than amplifier 170, but amplifier 182 can operate over the much larger temperature range of thirty-one degrees Centigrade (31° C.) to forty-five degrees Centigrade (45° C.). The output of amplifier 182 is sent to analog-to-digital converter 184 producing a digital output 186 having an accuracy of three degrees Centigrade (3° C.).

Figure 17:
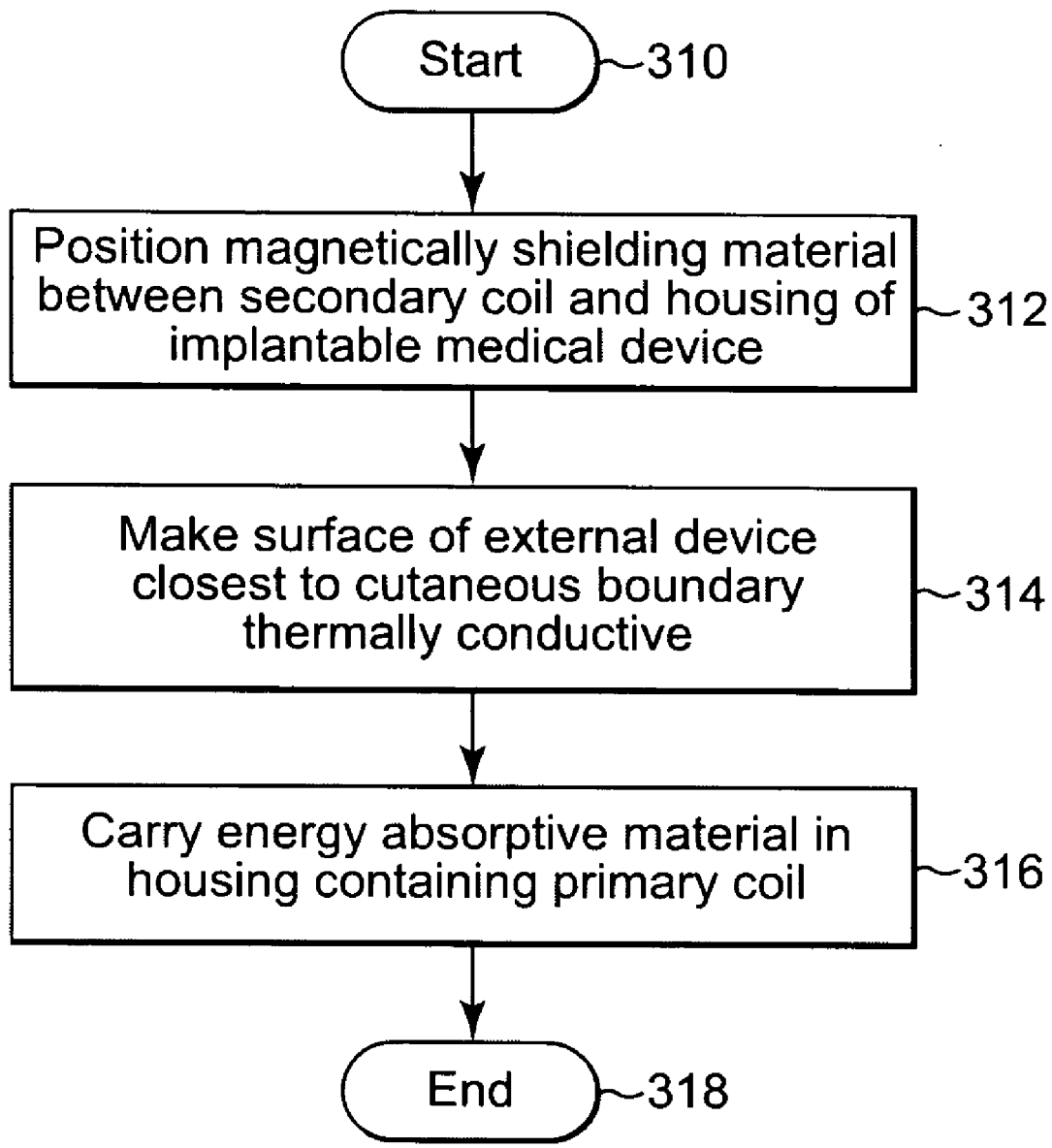
FIG. 17 is a flow chart illustrating a process incorporating an embodiment of the present invention.

FIG. 17 illustrates a process in accordance with a preferred embodiment of the present invention. The process starts (310) by positioning (312) a magnetically shielding material between secondary coil 34 and housing 32 of implantable medical device 16. The surface 90 of external antenna 52 closest to cutaneous boundary 38 is made thermally conductive (314). An energy absorptive material 60 is carried (316) in external antenna 52 containing primary coil 54. The process ends (318).

Some or all of the various features of implantable medical device 16 and charging unit 50 described enable a system for transcutaneous energy transfer having a relatively high efficiency of energy transfer, especially in situations involving some latitude of maladjustment of external antenna 52 with secondary coil 34. High efficiency of energy transfer can enable a rechargeable power source 24 of implantable medical device 16 to be charged, or recharged, within a shorter period of time than would otherwise be possible. Alternatively or in addition, high efficiency of energy transfer can enable transcutaneous energy transfer to occur at higher rate than would otherwise be possible since more of the energy generated by charging unit 50 is actually converted to charging rechargeable power source 24 instead of generating heat in implanted medical device 16 and/or surrounding tissue of patient 18. Alternatively or in addition, high efficiency of energy transfer can result in lower temperatures being imparted to implanted medical device 16 and/or surrounding tissue of patient 18. Alternatively or in addition, high efficiency of energy transfer can enable a greater degree of maladjustment of external antenna 52 with secondary coil 34 effectively resulting in patient 18 being able to be more ambulatory.

Thus, embodiments of the external power source for an implantable medical device having an adjustable magnetic core and system and method related thereto are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for transcutaneous energy transfer, comprising;

an implantable medical device, comprising:
  a first housing having operational componentry for providing said therapeutic output;
  a secondary housing mechanically coupled to said first housing having a secondary coil operatively coupled to said componentry, said secondary coil capable of receiving energy from said external source; and
  a magnetically shielding material positioned between said secondary coil and said first housing; and
an external power source, comprising:
  an external housing;
  a primary coil carried in said external housing, said primary coil being capable of inductively energizing said secondary coil when said housing is externally placed in proximity of said secondary coil with a first surface of said housing positioned closest to said secondary coil, said first surface of said housing being thermally conductive surface; and
  an energy absorptive material carried within said external housing.

2. A system for transcutaneous energy transfer as in claim 1 further comprising a temperature sensor thermally coupled to said thernialy conductive surface.

3. A system for transcutaneous energy transfer as in claim 2 wherein said temperature sensor is capable of indicating a temperature of said thermally conductive surface and further comprising circuitry coupled to said temperature sensor operative to limit said energizing at least in part as a function of said temperature.

4. A system for transcutaneous energy transfer as in claim 3 wherein said temperature sensor has a high resolution mode and a low resolution mode.

5. A system for transcutaneous energy transfer as in claim 4 wherein said external power source limits said energizing above a predetermined temperature of said thermally conductive surface and wherein said circuitry utilizes said high resolution mode of said temperature sensor when said temperature of said thermally conductive surface is within three degrees Celsius of said predetermined temperature and utilizes said low resolution mode of said temperature sensor when said temperature of said thermally conductive surface is outside of three degrees Celsius of said predetermined temperature.

6. A system for charging, comprising:
   an implantable medical device, comprising:
      a first housing having:
         a rechargeable power source; and
         operational componentry coupled to said rechargeable power source for providing said therapeutic output;
      a secondary housing mechanically coupled to said first housing having a secondary coil operatively coupled to said rechargeable power source, said secondary coil capable of receiving energy from said external source; and
      a magnetically shielding material positioned between said secondary coil and said fast housing; and
   an external charger, comprising:
      an external housing;
      a primary charging coil carried in said external housing, said primary charging coil being capable of inductively energizing said secondary coil when said housing is externally placed in proximity of said secondary coil with a first surface of said housing positioned closest to said secondary coil, said first surface of said housing being thermally conductive surface; and
      an energy absorptive material carried within said external housing.

7. A system for charging as in claim 6 further comprising a temperature sensor thermally coupled to said thermally conductive surface.

8. A system for charging as in claim 7 wherein said temperature sensor is capable of indicating a temperature of said thermally conductive surface and further comprising circuitry coupled to said temperature sensor operative to limit said energizing at least in part as a function of said temperature.

9. A system for charging as in claim 8 wherein said temperature sensor has a high resolution mode and a low resolution mode.

10. A system for charging as in claim 9 wherein said charger limits said energizing above a predetermined temperature of said thermally conductive surface and wherein said circuitry utilizes said high resolution mode of said temperature sensor when said temperature of said thermally conductive surface is within three degrees Celsius of said predetermined temperature and utilizes said low resolution mode of said temperature sensor when said temperature of said thermally conductive surface is outside of three degrees Celsius of said predetermined temperature.

11. An external power source for an implantable medical device having a secondary coil operatively coupled to therapeutic componentry, comprising:
   a housing;
   a primary coil carried in said housing, said primary coil being capable of inductively energizing said secondary coil when said housing is externally placed in proximity of said secondary coil with a first surface of said housing positioned closest to said secondary coil;
   said first surface of said housing being thermally conductive surface.

12. An external power source as in claim 11 further comprising a temperature sensor thermally coupled to said thermally conductive surface.

13. An external power source as in claim 12 wherein said temperature sensor is capable of indicating a temperature of said thermally conductive surface and further comprising circuitry coupled to said temperature sensor operative to limit said energizing at least in part as a function of said temperature.

14. An external power source as in claim 13 wherein said temperature sensor has a high resolution mode and a low resolution mode.

15. An external power source as in claim 14 wherein said external power source limits said energizing above a predetermined temperature of said thermally conductive surface and wherein said circuitry utilizes said high resolution mode of said temperature sensor when said temperature of said thermally conductive surface is within three degrees Celsius of said predetermined temperature and utilizes said low resolution mode of said temperature sensor when said temperature of said thermally conductive surface is outside of three degrees Celsius of said predetermined temperature.

16. An external power source for an implantable medical device having a secondary coil operatively coupled to therapeutic componentry, comprising:
   a housing;
   a primary coil carried in said housing, said primary coil being capable of inductively energizing said secondary coil when said housing is externally placed in proximity of said secondary coil with a first surface of said housing positioned closest to said secondary coil; and
   a temperature sensor thermally coupled to said first surface.

17. An external power source as in claim 16 wherein said temperature sensor has an accuracy within one-tenth of one degree Centigrade (1° C.) over at least a portion of a range of operation of said temperature sensor.

18. An external power source as in claim 16 wherein said temperature sensor has a high resolution mode and a low resolution mode.

19. An external power source as in claim 18 wherein said external power source limits said energizing above a predetermined temperature of said temperature sensor and wherein said circuitry utilizes said high resolution mode of said temperature sensor when said temperature of said temperature sensor is within three degrees Celsius of said predetermined temperature and utilizes said low resolution mode of said temperature sensor when said temperature of said temperature sensor is outside of three degrees Celsius of said predetermined temperature.

20. An external power source as in claim 16 wherein said temperature sensor is capable of indicating a temperature of said first surface and further comprising circuitry coupled to said temperature sensor operative to limit said energizing at least in part as a function of said temperature.

21. A charger for an implantable medical device having a rechargeable power source and a secondary coil operatively coupled to said rechargeable power source, comprising:
a housing;
a primary charging coil carried in said housing, said primary charging coil being capable of inductively energizing said secondary coil when said housing is externally placed in proximity of said secondary coil with a first surface of said housing positioned closest to said secondary coil;
said first surface of said housing being thermally conductive surface.

22. A charger as in claim 21 further comprising a temperature sensor thermally coupled to said thermally conductive surface.

23. A charger as in claim 22 wherein said temperature sensor is capable of indicating a temperature of said thermally conductive surface and further comprising circuitry coupled to said temperature sensor operative to limit said energizing at least in part as a function of said temperature.

24. A charger as in claim 23 wherein said temperature sensor has a high resolution mode and a low resolution mode.

25. A charger as in claim 24 wherein said charger limits said energizing above a predetermined temperature of said thermally conductive surface and wherein said circuitry utilizes said high resolution mode of said temperature sensor when said temperature of said thermally conductive surface is within three degrees Celsius of said predetermined temperature and utilizes said low resolution mode of said temperature sensor when said temperature of said thermally conductive surface is outside of three degrees Celsius of said predetermined temperature.

26. A system of transcutaneous energy transfer, comprising:
an implantable medical device having a secondary coil operatively coupled to therapeutic componentry;
an external power source comprising:
a housing;
a primary coil carried in said housing, said primary coil being capable of inductively energizing said secondary coil when said housing is externally placed in proximity of said secondary coil with a first surface of said housing positioned closest to said secondary coil;
said first surface of said housing being thermally conductive surface.

27. A system as in claim 26 further comprising a temperature sensor thermally coupled to said thermally conductive surface.

28. A system as in claim 27 wherein said temperature sensor is capable of indicating a temperature of said thermally conductive surface and further comprising circuitry coupled to said temperature sensor operative to limit said energizing at least in part as a function of said temperature.

29. A system as in claim 28 wherein said temperature sensor has a high resolution mode and a low resolution mode.

30. A system as in claim 29 wherein said external power source limits said energizing above a predetermined temperature of said thermally conductive surface and wherein said circuitry utilizes said high resolution mode of said temperature sensor when said temperature of said thermally conductive surface is within three degrees Celsius of said predetermined temperature and utilizes said low resolution mode of said temperature sensor when said temperature of said thermally conductive surface is outside of three degrees Celsius of said predetermined temperature.

31. A system of charging, comprising:
an implantable medical device having a rechargeable power source and a secondary coil operatively coupled to said rechargeable power source;
an external power source comprising:
a housing;
a primary coil carried in said housing, said primary coil being capable of inductively energizing said secondary coil when said housing is externally placed in proximity of said secondary coil with a first surface of said housing positioned closest to said secondary coil;
said first surface of said housing being thermally conductive surface.

32. A system as in claim 31 further comprising a temperature sensor thermally coupled to said thermally conductive surface.

33. A system as in claim 32 wherein said temperature sensor is capable of indicating a temperature of said thermally conductive surface and further comprising circuitry coupled to said temperature sensor operative to limit said energizing at least in part as a function of said temperature.

34. A system as in claim 33 wherein said temperature sensor has a high resolution mode and a low resolution mode.

35. A system as in claim 34 wherein said external power source limits said energizing above a predetermined temperature of said thermally conductive surface and wherein said circuitry utilizes said high resolution mode of said temperature sensor when said temperature of said thermally conductive surface is within three degrees Celsius of said predetermined temperature and utilizes said low resolution mode of said temperature sensor when said temperature of said thermally conductive surface is outside of three degrees Celsius of said predetermined temperature.

36. An external power source for an implantable medical device having a secondary coil operatively coupled to therapeutic componentry, comprising:
a housing;
a primary coil carried in said housing, said primary coil being capable of inductively energizing said secondary coil when placed in proximity of said secondary coil; and
an energy absorptive material carried within said housing.

37. An external power source as in claim 36 wherein said energy absorptive material changes state at a temperature near an operating temperature of said housing during operation of said charger.

38. An external power source as in claim 37 wherein said energy absorptive material comprises wax.

39. A charger for an implantable medical device having a rechargeable power source and a secondary coil operatively coupled to said rechargeable power source, comprising:
a housing;
a primary charging coil carried in said housing, said primary charging coil being capable of inductively energizing said secondary coil when placed in proximity of said secondary coil; and
an energy absorptive material carried within said housing.

40. A charger as in claim 39 wherein said energy absorptive material changes state at a temperature near an operating temperature of said housing during operation of said charger.

41. A charger as in claim 40 wherein said energy absorptive material comprises wax.

42. A system for transcutaneous energy transfer, comprising:
- an inplantable medical device having a secondary coil operatively coupled to therapeutic componentry;
- an external power source, comprising:
  - a housing;
  - a primary coil carried in said housing, said primary coil being capable of inductively energizing said secondary coil when placed in proximity of said secondary coil; and
  - an energy absorptive material carried within said housing.

43. A system as in claim 42 wherein said energy absorptive material changes state at a temperature near an operating temperature of said housing during operation of said charger.

44. A system as in claim 43 wherein said energy absorptive material comprises wax.

45. A method of transcutaneous energy transfer from an external power source comprising an external housing and a primary coil carried in said external housing, said primary coil being capable of inductively energizing said secondary coil when said housing is externally placed in proximity of said secondary coil with a first surface of said housing positioned closest to said secondary coil to an implantable medical device comprising a first housing having operational componentry for providing said therapeutic output and a secondary housing mechanically coupled to said first housing having a secondary coil operatively coupled to said componentry, said secondary coil capable of receiving energy from said external source, comprising the steps of:

- positioning a magnetically shielding material between said secondary coil and said first housing;
- making said first surface of said housing thermally conductive; and
- carrying an energy absorptive material within said external housing.

46. A method as in claim 45 further comprising the step of coupling a temperature sensor thermally to said thermally conductive surface.

47. A method as in claim 46 wherein said temperature sensor is capable of indicating a temperature of said thermally conductive surface and further comprising circuitry coupled to said temperature sensor operative to limit said energizing at least in part as a function of said temperature.

48. A method as in claim 47 wherein said temperature sensor has a high resolution mode and a low resolution mode.

49. A method as in claim 48 wherein said external power source limits said energizing above a predetermined temperature of said thermally conductive surface and wherein said circuitry utilizes said high resolution mode of said temperature sensor when said temperature of said thermally conductive surface is within three degrees Celsius of said predetermined temperature and utilizes said low resolution mode of said temperature sensor when said temperature of said thermally conductive surface is outside of three degrees Celsius of said predetermined temperature.

* * * * *

UNITED STATES PATENT AND TRADEMARK OFFICE
CERTIFICATE OF CORRECTION

PATENT NO. : 7,225,032 B2
APPLICATION NO. : 10/836101
DATED : May 29, 2007
INVENTOR(S) : Schmeling et al.

It is certified that error appears in the above-identified patent and that said Letters Patent is hereby corrected as shown below:

Col. 22, Line 64: "said thernialy" should read --said thermally--

Col. 23, Line 32: "said fast housing" should read --said first housing--

Signed and Sealed this

Twenty-seventh Day of November, 2007

JON W. DUDAS
*Director of the United States Patent and Trademark Office*